(12) United States Patent
Yukawa et al.

(10) Patent No.: US 8,426,172 B2
(45) Date of Patent: Apr. 23, 2013

(54) TRANSFORMANT CAPABLE OF PRODUCING ISOPROPANOL

(75) Inventors: Hideaki Yukawa, Kyoto (JP); Masayuki Inui, Kyoto (JP)

(73) Assignee: Research Institute of Innovation Technology for the Earth, Kyoto (JP)

( * ) Notice: Subject to any disclaimer, the term of this patent is extended or adjusted under 35 U.S.C. 154(b) by 495 days.

(21) Appl. No.: 12/733,366

(22) PCT Filed: Aug. 28, 2008

(86) PCT No.: PCT/JP2008/065355
§ 371 (c)(1), (2), (4) Date: Apr. 8, 2010

(87) PCT Pub. No.: WO2009/028582
PCT Pub. Date: Mar. 5, 2009

(65) Prior Publication Data
US 2010/0203604 A1    Aug. 12, 2010

(30) Foreign Application Priority Data
Aug. 29, 2007   (JP) ................................ 2007-222633

(51) Int. Cl.
C12P 7/04 (2006.01)
C12N 1/21 (2006.01)

(52) U.S. Cl.
USPC .................... 435/157; 435/252.3; 435/252.33

(58) Field of Classification Search .................. 435/157, 435/252.3, 252.33
See application file for complete search history.

(56) References Cited

U.S. PATENT DOCUMENTS
2008/0293125 A1* 11/2008 Subbian et al. ............ 435/252.3

FOREIGN PATENT DOCUMENTS
WO    2008/131286    10/2008

OTHER PUBLICATIONS

Blast2, NCBI web site, of instant SEQ ID Nos. 13-16 vs. SEQ ID No. 1 or 2 of Subbian et al., US 2008/0293125 A1, http://blast.ncbi.nlm.nih.gov/Blast.cgi, performed on Sep. 21, 2012.*
Supplementary European Search Report dated Dec. 1, 2010 in Application No. EP 08 82 8643.
R. Yan et al., "Expression of Solvent-Forming Enzymes and Onset of Solvent Production in Batch Cultures of *Clostridium beijerinckii* ("*Clostridium butylicum*")", Applied and Environmental Microbiology, vol. 54, No. 3, pp. 642-648, Mar. 1988.
L. L. Bermejo et al., "Expression of *Clostridium acetobutylicum* ATCC 824 Genes in *Escherichia coli* for Acetone Production and Acetate Detoxification", Applied and Environmental Microbiology, vol. 64, No. 3, pp. 1079-1085, Mar. 1998.
A. A. Ismaiel et al., "Purification and Characterization of a Primary-Secondary Alcohol Dehydrogenase from Two Strains of *Clostridium beijerinckii*", Journal of Bacteriology, vol. 175, No. 16, pp. 5097-5105, Aug. 1993.

(Continued)

*Primary Examiner* — Rosanne Kosson
(74) *Attorney, Agent, or Firm* — Wenderoth, Lind & Ponack, L.L.P.

(57) ABSTRACT

A transformant capable of producing isopropanol which is constructed by transferring the following genes (a) to (d) into an aerobic bacterium or a facultative anaerobic bacterium:
(a) a foreign gene which encodes an enzyme having acetyl-CoA acetyltransferase activity;
(b) a foreign gene which encodes an enzyme having acetoacetyl CoA:acetate CoA-transferase activity;
(c) a foreign gene which encodes an enzyme having acetoacetate decarboxylase activity; and
(d) a foreign gene which encodes an enzyme having isopropanol dehydrogenase activity.

4 Claims, 2 Drawing Sheets

OTHER PUBLICATIONS

J. Toth et al., "*Clostridium beijerinckii* stain NRRL B593 Putative Transcription Activator (stc), NADP-Dependent Alcohol Dehydrogenase (adh), and Putative Electron-Transfer Protein (hydG) Genes, complete cds; and Putative Glutamate Synthase Small Subunit(gltD) Gene, Partial cds", Database Genbank, Mar. 9, 2005, XP002607790, Database Accession No. AF157307.

P. Durre, "New Insights and Novel Developments in Clostridial Acetone/Butanol/Isopropanol Fermentation", Applied Microbiology and Biotechnology, vol. 49, No. 6, pp. 639-648, Jan. 1, 1998.

International Search Report issued Dec. 2, 2008 in International (PCT) Application No. PCT/JP2008/065355.

W. J. Mitchell, "Physiology of Carbohydrate to Solvent Conversion by Clostridia", Advances in Microbial Physiology, vol. 39, pp. 31-130, 1997.

K. P. Stim-Herndon et al., "Characterization of an Acety-CoA C-Acetyltransferase (thiolase) gene from *Clostridium acetobutylicum* ATCC 824", Gene, vol. 154, pp. 81-95, 1995.

D. J. Petersen et al., "Sequence and Arrangement of Genes Encoding Enzymes of the Acetone-Production Pathway of *Clostridium acetobutylicum* ATCC 824", Gene, 123, pp. 93-97, 1993.

Database DDBJ/EMBL/GenBank [online], Accession No. AF157307, http://www.ncbi.nlm.nih.gov/entrez/viewer.fcgi?db=nuccore&id=60592972, Mar. 9, 2005 uploaded, Toth, J. et al.

T. Hanai et al., "Engineered Synthetic Pathway for Isopropanol Production in *Escherichia coli*", Applied and Environmental Microbiology, vol. 73, No. 24, pp. 7814-7818, Dec. 2007.

T. Jojima et al., "Production of Isopropanol by Metabolically Engineered *Escherichia coli*", Appl. Microbiol Biotechnol., vol. 77, pp. 1219-1224, 2008.

English Translation of the International Preliminary Report on Patentability.

* cited by examiner

TRANSFORMANT CAPABLE OF PRODUCING ISOPROPANOL

This application is a U.S. national stage of International Application No. PCT/JP2008/065355 filed Aug. 28, 2008.

TECHNICAL FIELD

The present invention relates to technique for producing isopropanol. In more detail, the present invention relates to a transformant of an aerobic bacterium or a facultative anaerobic bacterium which has undergone specific gene manipulation so as to be provided with an isopropanol producing function, and relates to an efficient isopropanol producing technique using the transformant.

BACKGROUND ART

Isopropanol, as an industrial solvent for paints, inks, or the like, or as an industrial material for various uses, is currently produced in an amount of about 1,800,000 tons per year worldwide and about 180,000 tons per year in Japan. Also, isopropanol can be converted into propylene by simple dehydration, and therefore can be used as a source of polypropylene, which is currently produced in an amount of about 3,100,000 tons per year in Japan.

However, these products are all derived from fossil crude resources.

Development of new methods for producing energy or chemical products not from fossil resources, almost all of which is imported, but from renewable resources is strongly desired in order to solve global environmental issues such as global warming, exhaustion of fossil resources, and soaring oil prices, and to reduce the dependence on foreign countries for important raw material resources for chemical products. Efficient technique for producing isopropanol from renewable resources, such as biomass, would be one of the measures to solve these problems.

As an example of microbial production of isopropanol from biomass resources, it is reported that a kind of *Clostridium* that performs acetone-butanol fermentation produces isopropanol in addition to butanol (isopropanol-butanol fermentation). This is because the *Clostridium* exhibiting such a fermentation pattern has isopropanol dehydrogenase, which reduces acetone to isopropanol as a catalyst.

In recent years, the production and use of biofuel is increasing around the world, and from the standpoint of biofuel production, researches on butanol production based on acetone-butanol fermentation are attracting attention again. However, these researches are primarily intended for butanol production, and few of them are intended for isopropanol production.

As bacteria which produce isopropanol, *Clostridium* bacteria, known as isopropanol-butanol fermenting bacteria, such as *Clostridium beijerinckii, Clostridium aurantibutyricum, Clostridium butyricum,* etc. have been reported so far (Applied and Environmental Microbiology, Vol. 45, 1983, 1160-1163).

However, isopropanol production using *Clostridium* bacteria has the following problems.

(1) In isopropanol-butanol fermentation by *Clostridium* bacteria, butanol is the main fermentation metabolite, and isopropanol is produced in low efficiency. Specifically, the ratio of isopropanol/butanol produced by *Clostridium* bacteria is about 1/5 to 1/10.

(2) *Clostridium* bacteria require strictly anaerobic conditions in proliferation and in production of isopropanol. Therefore, for such strictly anaerobic conditions, complicated culture procedure involving, for example, replacement of the air in the culture apparatus with an inert gas such as nitrogen gas, is required. In addition, the proliferation rate of the bacteria is extremely low, and as a result, the isopropanol production rate is low. To solve these problems, use of aerobic bacteria with a high proliferation rate may be considered, but no microorganism (an aerobic bacterium or a facultative anaerobic bacterium) that can proliferate under aerobic conditions and produce isopropanol with high efficiency has yet been known.

(3) In isopropanol-butanol fermentation, acetic acid and butyric acid are generated during cell-growth phase, and during stationary phase, in which cell growth stops, acidification to lower pH in fermentation culture triggers transition to solvent (isopropanol and butanol)-production phase, resulting in a drastic change in metabolic system (catabolic shift) and production of isopropanol and butanol. Thus, isopropanol-butanol fermentation requires strict control of the fermentation process, and substantial time from the start of fermentation to the production of isopropanol and butanol. Also, these *Clostridium* bacteria have problems including that transition to sporulation phase stops the production of isopropanol and butanol, that is, the production of isopropanol does not last long.

Therefore, in order to solve these problems, creation of a novel isopropanol-producing microorganism and invention of a novel isopropanol-producing process are desired.

For producing isopropanol with the use of *Clostridium* bacteria, the following techniques have been disclosed.

Applied and Environmental Microbiology, Vol. 45, 1983, 1160-1163 discloses that *Clostridium beijerinckii* produces isopropanol in addition to butanol and that *Clostridium aurantibutyricum* produces isopropanol in addition to butanol and acetone.

Also, Enzyme and Microbial Technology, Vol. 5, 1983, 46-54 and Biotechnology and Bioengineering, Vol. 39, 1992, 148-156 disclose a continuous isopropanol-producing technique using immobilized *Clostridium* bacteria; Applied Microbiology and Biotechnology, Vol. 32, 1989, 22-26 discloses an isopropanol-producing technique using agglutinating *Clostridium* bacteria; Applied Microbiology and Biotechnology, Vol. 25, 1986, 29-31 discloses a technique of reducing product inhibition in isopropanol-butanol fermentation mediated by *Clostridium* bacteria, by adding a polymer resin to adsorb products, which are isopropanol and butanol. However, the focus of these techniques is producing butanol, and they are all isopropanol-producing techniques using *Clostridium* bacteria under anaerobic conditions. Therefore, they are not fundamental solutions to the problems pointed out in the above (1), (2), (3), etc.

Meanwhile, although not for isopropanol production, the following acetone-butanol producing techniques using *Clostridium* bacteria have been disclosed so far.

WO 2006/007530 discloses a technique of controlling a gene responsible for sporulation to delay sporulation phase for increasing butanol production; US 2005/089979 A1 and Bioprocess and Biosystems Engineering, Vol. 27, 2005, 207-214 disclose a technique of continuous extraction of butanol by the gas-stripping method in continuous fermentation; Pakistan Journal of Biological Sciences, Vol. 9, 2006, 1923-1928 and Applied Biochemistry and Biotechnology, Vol. 113-116, 2004, 887-898 disclose a butanol-producing technique by immobilizing *Clostridium* bacteria; Journal of Biotechnology, Vol. 120, p197-206 discloses a technique of recycling bacteria cells in continuous fermentation by using high-density *Clostridium* bacteria. Although these techniques are considered to be applicable to isopropanol-butanol fermentation as well using *Clostridium* bacteria, they are nothing but production techniques using *Clostridium* bacteria under anaerobic Conditions, and therefore not fundamental solutions to the above-mentioned problems.

SUMMARY OF INVENTION

Technical Problem

An object of the present invention is to provide a recombinant microorganism capable of producing isopropanol from renewable resources, and a method for efficiently producing isopropanol using the microorganism.

Solution to Problem

The present inventors made extensive examination to solve the problem described above, and found that isopropanol is efficiently produced by transformants created by transferring a foreign gene which encodes an enzyme having acetyl-CoA acetyltransferase activity, a foreign gene which encodes an enzyme having acetoacetyl-CoA:acetate CoA-transferase activity, a foreign gene which encodes an enzyme having acetoacetate decarboxylase activity, and a foreign gene which encodes an enzyme having isopropanol dehydrogenase activity, into an aerobic bacterium or a facultative anaerobic bacterium. Such recombinant microorganisms can efficiently produce isopropanol because they are microorganisms (aerobic bacteria or facultative anaerobic bacteria) capable of proliferation under aerobic conditions, which have a high isopropanol production rate due to their high proliferation rate, whereas conventional isopropanol-producing bacteria, *Clostridium*, need strictly anaerobic conditions in proliferation and isopropanol production and therefore have a low isopropanol production rate due to their low proliferation rate. For this reason, the transformant of the present invention enables efficient isopropanol production, and accordingly easy design and operation of an isopropanol production process. The present invention, which has been completed based on the above-mentioned findings, provides the following microorganism and a method for producing isopropanol using the microorganism.

(1) A transformant capable of producing isopropanol, which is constructed by transferring the following genes (a) to (d) into an aerobic bacterium or a facultative anaerobic bacterium:
(a) a foreign gene which encodes an enzyme having acetyl-CoA acetyltransferase activity;
(b) a foreign gene which encodes an enzyme having acetoacetyl CoA:acetate CoA-transferase activity;
(c) a foreign gene which encodes an enzyme having acetoacetate decarboxylase activity; and
(d) a foreign gene which encodes an enzyme having isopropanol dehydrogenase activity.
(2) The transformant according to the above (1), wherein
(a) the foreign gene which encodes an enzyme having acetyl-CoA acetyltransferase activity is a DNA comprising the base sequence of SEQ ID NO: 13, or a DNA which hybridizes to a DNA comprising the base sequence of SEQ ID NO: 13 or a complementary base sequence of SEQ ID NO: 13 under stringent conditions and which encodes a polypeptide having acetyl-CoA acetyltransferase activity;
(b) the foreign gene which encodes an enzyme having acetoacetyl CoA:acetate CoA-transferase activity is a DNA comprising the base sequence of SEQ ID NO: 14, or a DNA which hybridizes to a DNA comprising the base sequence of SEQ ID NO: 14 or a complementary base sequence of SEQ ID NO: 14 under stringent conditions and which encodes a polypeptide having acetoacetyl CoA:acetate CoA-transferase activity;
(c) the foreign gene which encodes an enzyme having acetoacetate decarboxylase activity is a DNA comprising the base sequence of SEQ ID NO: 15, or a DNA which hybridizes to a DNA comprising the base sequence of SEQ ID NO: 15 or a complementary base sequence of SEQ ID NO: 15 under stringent conditions and which encodes a polypeptide having acetoacetate decarboxylase activity; and
(d) the foreign gene which encodes an enzyme having isopropanol dehydrogenase activity is a DNA comprising the base sequence of SEQ ID NO: 16, or a DNA which hybridizes to a DNA comprising the base sequence of SEQ ID NO: 16 or a complementary base sequence of SEQ ID NO: 16 under stringent conditions and which encodes a polypeptide having isopropanol dehydrogenase activity.
(3) The transformant according to the above (1) or (2), wherein the aerobic bacterium or facultative anaerobic bacterium is *Escherichia coli*.
(4) The transformant according to the above (1), wherein (a) the foreign gene which encodes an enzyme having acetyl-CoA acetyltransferase activity, (b) the foreign gene which encodes an enzyme having acetoacetyl CoA:acetate CoA-transferase activity, (c) the foreign gene which encodes an enzyme having acetoacetate decarboxylase activity, and (d) the foreign gene which encodes an enzyme having isopropanol dehydrogenase activity are a thl gene, a ctfAB gene, an adc gene, and an adh gene, respectively, derived from a same or different microorganism selected from the group consisting of *Clostridium beijerinckii*, *Clostridium aurantibutyricum*, *Clostridium acetobutylicum*, *Clostridium saccharoperbutylacetonicum*, *Clostridium saccharoacetobutylicum*, *Clostridium pasteurianum*, *Clostridium sporogenes*, *Clostridium cadaveris*, *Clostridium tetanomorphum*, and *Ralstonia eutropha*.
(5) The transformant according to the above (1), which is *Escherichia coli* JM109/pCRC201 (Accession Number: FERM BP-10978) or *Escherichia coli* JM109/pCRC202 (Accession Number FERM BP-10979).
(6) A method for producing isopropanol, which comprises a step of culturing the transformant according to any one of the above (1) to (5) in a culture medium containing saccharides, and a step of collecting isopropanol from a culture thereof.

Advantageous Effects of Invention

The transformant of the present invention is capable of extremely efficient production of isopropanol from saccharides.

The present invention enables efficient isopropanol production from renewable resources and construction of a new process for industrially producing isopropanol without depending on petroleum resources.

DETAILED DESCRIPTION OF THE INVENTION

Figure 1:
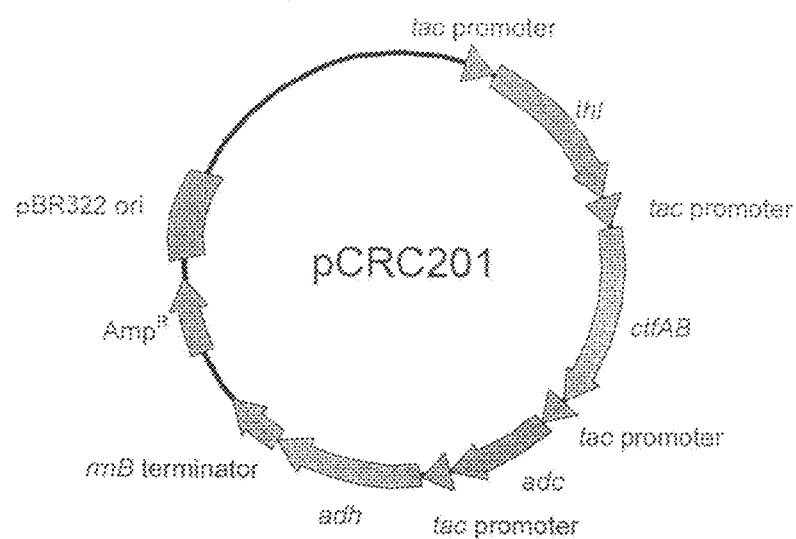
FIG. 1 shows the plasmid pCRC201 prepared in Example 1 (3).

Hereinafter, the present invention will be described in detail.

(I) Transformant Capable of Producing Isopropanol

The transformant of the present invention capable of producing isopropanol is a transformant, which is constructed by transferring the following genes (a) to (d) into an aerobic bacterium or a facultative anaerobic bacterium:
(a) a foreign gene which encodes an enzyme having acetyl-CoA acetyltransferase activity;
(b) a foreign gene which encodes an enzyme having acetoacetyl CoA:acetate CoA-transferase activity;
(c) a foreign gene which encodes an enzyme having acetoacetate decarboxylase activity; and
(d) a foreign gene which encodes an enzyme having isopropanol dehydrogenase activity.

Host

The host subjected to transformation in the present invention is not particularly limited as long as it is an aerobic bacterium or a facultative anaerobic bacterium capable of being transformed by a recombinant vector comprising a group of isopropanol production-related genes, allowing expression of isopropanol production-related enzymes encoded by the genes, and producing isopropanol as a result. Examples of the host include bacteria such as *Escherichia coli*, coryneform bacteria, *Streptococcus*, *Staphylococcus*, *Enterococcus*, *Bacillus* (for example, *Bacillus subtilis* etc.) and *Streptomyces*; fungus cells such as *Aspergillus*; yeast cells such as baker's yeast and *Pichia pastoris*; and competent cells thereof.

*Escherichia coli* and coryneform bacteria are preferred. Inter alia, preferable cell strains of *Escherichia coli* include *Escherichia coli* B, W3110, W3100, CSHS0, JM105, JM109, DH1, MC1060 and HB101.

The coryneform bacteria is a group of microorganisms defined in Bargeys Manual of Determinative Bacteriology, Vol. 8, 599 (1974), and is not particularly limited as long as it proliferates under normal aerobic conditions. The specific examples include *Corynebacterium*, *Brevibacterium*, *Arthrobacter*, *Mycobacterium* and *Micrococcus*.

Further specifically, examples of the *Corynebacterium* in the coryneform bacteria include *Corynebacterium glutamicum* R (FERM P-18976), ATCC13032, ATCC13058, ATCC13059, ATCC13060, ATCC13232, ATCC13286, ATCC13287, ATCC13655, ATCC13745, ATCC13746, ATCC13761, ATCC14020 and ATCC31831.

Examples of the *Brevibacterium* include *Brevibacterium lactofermentum* ATCC13869; *Brevibacterium flavum* MJ-233 (FERM BP-1497) and MJ-233AB-41 (FERM BP-1498); and *Brevibacterium* ammoniagenes ATCC6872.

Examples of the *Arthrobacter* include *Arthrobacter globiformis* ATCC8010, ATCC4336, ATCC21056, ATCC31250, ATCC31738 and ATCC35698.

Examples of the *Mycobacterium* include *Mycobacterium bovis* ATCC19210 and ATCC27289.

Examples of the *Micrococcus* include *Micrococcus freudenreichii* NO. 239 (FERM P-13221), *Micrococcus leuteus* NO. 240 (FERM P-13222), *Micrococcus ureae* IAM1010, and *Micrococcus roseus* IFO3764.

The *Escherichia coli* and the coryneform bacteria may be, let alone a wild strain, a mutant thereof or an artificial recombinant thereof. Examples of such *Escherichia coli* include disruptants of the respective genes encoding lactate dehydrogenase, fumarate reductase, and formate dehydrogenase. Examples of such coryneform bacteria include disruptants of the respective genes encoding lactate dehydrogenase, phosphoenolpyruvate carboxylase, and malate dehydrogenase.

Isopropanol production-related genes

As the above (a) to (d) isopropanol production-related genes, when the base sequences of DNA fragments comprising these genes are known, DNA fragments synthesized according to the sequences may be used. Even when the DNA sequences are unknown, necessary fragments can be obtained by a hybridization method and the PCR method based on amino acid sequences conserved among isopropanol production-related enzyme proteins. Also, such fragments can be obtained by degenerate PCR using mixed primers designed based on other known isopropanol production-related gene sequences.

In the above (a) to (d) isopropanol production-related genes, as long as their isopropanol-producing activity is maintained, a part of the base sequence may be substituted or deleted. Also, a base may be newly inserted, and a part of the base sequence may be transposed. Any of these derivatives may be used in the present invention. The above-mentioned "a part" may be, for example, one to several (1 to 5, preferably 1 to 3, and more preferably 1 to 2) in terms of amino-acid residues.

An isopropanol-producing bacterium usually carries the above (a) to (d) genes. Examples of the isopropanol-producing bacterium include *Clostridium* bacteria known to perform butanol-isopropanol fermentation, such as *Clostridium beijerinckii* and *Clostridium aurantibutyricum* (George, H. A. et al., Acetone, Isopropanol, and Butanol Production by *Clostridium beijerinckii* (syn. *Clostridium butylicum*) and *Clostridium aurantibutyricum*. Appl. Environ. Microbiol. 45:1160-1163 (1983)), and it has already been reported that isopropanol is produced from acetyl-CoA through a 4-step reaction (Mitchell, W. J., Physiology of carbohydrate to solvent conversion by clostridia. Adv. Microb. Physiol. 39:31-130 (1998)).

In particular, the isopropanol-producing pathway or the metabolic pathway from acetyl-CoA to isopropanol in the above *Clostridium* bacteria involves acetyl-CoA acetyltransferase (also known as thiolase) (hereinafter the gene and the enzyme will be abbreviated to "thl" and "THL", respectively) that catalyzes the reaction from acetyl-CoA to acetoacetyl-CoA, acetoacetyl CoA: acetate CoA transferase (hereafter the gene and the enzyme will be abbreviated to "ctfAB" and "CTF", respectively) that catalyzes the reaction from acetoacetyl-CoA to acetoacetate, acetoacetate decarboxylase (hereafter the gene and the enzyme will be abbreviated to "adc" and "ADC", respectively) that catalyzes the reaction from acetoacetate to acetone, and isopropanol dehydrogenase (also known as primary-secondary alcohol dehydrogenase) (hereafter the gene and the enzyme will be abbreviated to "adh" and "ADH", respectively) that catalyzes the reaction from acetone to isopropanol.

The present invention uses this metabolic system. The kind and combination of the microorganism of origin, the order of transfer, etc. of the above (a) to (d) genes are not limited as long as the isopropanol-producing function is maintained.

The above (a) to (d) genes may be obtained from bacteria incapable of producing isopropanol. The specific examples include the following.

As *Clostridium* bacteria which do not produce isopropanol but perform butanol-acetone fermentation, *Clostridium acetobutylicum*, *Clostridium saccharoperbutylacetonicum*, *Clostridium saccharoacetobutylicum*, *Clostridium pasteurianum*, *Clostridium sporogenes*, *Clostridium cadaveris*, *Clostridium tetanomorphum*, etc. have been reported (George, H. A. et al., Acetone, Isopropanol, and Butanol Production by *Clostridium* beijerinckii (syn. *Clostridium*

*butylicum*) and *Clostridium* aurantibutyricum. Appl. Environ. Microbiol. 45:1160-1163 (1983)). It has been reported that these *Clostridium* bacteria which perform butanol-acetone fermentation have the genes which encode enzymes for the three steps from acetyl-CoA to acetone (THL, CTF and ADC) for acetone production (Noelling, J. et al., Genome sequence and comparative analysis of the solvent-producing bacterium *Clostridium acetobutylicum*. J. Bacteriol. 183:4823-4838). Therefore, instead of or in addition to the THL-encoding gene, the CTF-encoding gene, and the ADC-encoding gene derived from *Clostridium beijerinckii* and/or *Clostridium aurantibutyricum* that perform butanol-isopropanol fermentation, a THL-encoding gene, a CTF-encoding gene, and an ADC-encoding gene derived from the above-mentioned *Clostridium* bacteria that perform butanol-acetone fermentation may be used, respectively.

Since genomes of more than 600 species have been sequenced so far, it has come to be possible to extract information on a target gene derived from various species and to isolate the gene, based on homology search using gene databases. Therefore, a THL-encoding gene, a CTF-encoding gene, an ADC-encoding gene and an ADH-encoding gene derived from species other than the above-mentioned *Clostridium* bacteria can also be easily isolated. Among such isopropanol production-related genes, those of relatively high homology with the corresponding genes derived from the above-mentioned *Clostridium* bacteria will be exemplified below. Examples of THL-encoding genes include, for example, THL-encoding genes derived from *Clostridium perfringens, Clostridium tetani, Clostridium kluyveri, Clostridium butyricum, Clostridium novyi, Clostridium botulinum, Thermoanaerobacterium thermosaccharolyticum, Thermosinus carboxydivorans, Clostridium difficile, Carboxydothermus hydrogenoformans, Thermoanaerobacter tengcongensis, Desulfotomaculum reducens, Oceanospirillum* sp., *Pseudomonas putida*, etc. Examples of CTF-encoding genes include those derived from *Thermoanaerobacter tengcongensis, Escherichia coli* K12, etc. Examples of ADC-encoding genes include those derived from *Saccharopolyspora erythraea, Streptomyces nogalater, Pseudomonas aeruginosa, Streptomyces avermitilis*, etc. Examples of ADH-encoding genes include those derived from *Thermoanaerobacter ethanolicus, Thermoanaerobacter tengcongensis, Thermoanaerobacter brockii, Thermosinus carboxydivorans, Methanosarcina barkeri*, etc. Therefore, instead of or in addition to the THL-encoding gene, the CTF-encoding gene, the ADC-encoding gene and the ADH-encoding gene derived from the above-mentioned *Clostridium* bacteria that perform butanol-isopropanol fermentation or butanol-acetone fermentation, a THL-encoding gene, a CTF-encoding gene, an ADC-encoding gene and an ADH-encoding gene derived from, for example, other species mentioned in this paragraph may be used, respectively as long as the catalytic activity of an enzyme encoded by each gene is the same as that of the corresponding enzyme.

In the present invention, it is preferred to use, as the above (a) to (d) genes, a thl gene, a ctfAB gene, an adc gene, and an adh gene, respectively, derived from the same or different microorganism selected from the group consisting of *Clostridium beijerinckii, Clostridium aurantibutyricum, Clostridium acetobutylicum, Clostridium saccharoperbutylacetonicum, Clostridium saccharoacetobutylicum, Clostridium pasteurianum, Clostridium sporogenes, Clostridium cadaveris, Clostridium tetanomorphum,* and *Ralstonia eutropha*.

In the present invention, it is most preferred to use, as the above (a) to (d) genes, the THL-encoding gene, the CTF-encoding gene, and the ADC-encoding gene derived from *Clostridium acetobutylicum*, and the ADH-encoding gene derived from *Clostridium beijerinckii*.

In the present invention, it is preferred that (a) the foreign gene which encodes an enzyme having acetyl-CoA acetyltransferase activity is a DNA comprising the base sequence of SEQ ID NO: 13, or a DNA which hybridizes to a DNA comprising the base sequence of SEQ ID NO: 13 or a complementary base sequence of SEQ ID NO: 13 under stringent conditions and which encodes a polypeptide having acetyl-CoA acetyltransferase activity;

(b) the foreign gene which encodes an enzyme having acetoacetyl CoA:acetate CoA-transferase activity is a DNA comprising the base sequence of SEQ ID NO: 14, or a DNA which hybridizes to a DNA comprising the base sequence of SEQ ID NO: 14 or a complementary base sequence of SEQ ID NO: 14 under stringent conditions and which encodes a polypeptide having acetoacetyl CoA:acetate CoA-transferase activity;

(c) the foreign gene which encodes an enzyme having acetoacetate decarboxylase activity is a DNA comprising the base sequence of SEQ ID NO: 15, or a DNA which hybridizes to a DNA comprising the base sequence of SEQ ID NO: 15 or a complementary base sequence of SEQ ID NO: 15 under stringent conditions and which encodes a polypeptide having acetoacetate decarboxylase activity; and (d) the foreign gene which encodes an enzyme having isopropanol dehydrogenase activity is a DNA comprising the base sequence of SEQ ID NO: 16, or a DNA which hybridizes to a DNA comprising the base sequence of SEQ ID NO: 16 or a complementary base sequence of SEQ ID NO: 16 under stringent conditions and which encodes a polypeptide having isopropanol dehydrogenase activity.

The DNAs of the base sequences of SEQ ID NOs: 13 to 15 are genes derived from *Clostridium acetobutylicum*. SEQ ID NO: 13, 14 and 15 are the base sequences of the thl gene, the ctfAB gene, and the adc gene, respectively. The DNA of the base sequence of SEQ ID NO: 16 is the adh gene derived from *Clostridium beijerinckii*.

The "stringent conditions" as used herein means general conditions, for example, the conditions described in J. Sambrook et al., Molecular Cloning, A Laboratory Manual, Second edition, Cold Spring Harbor Laboratory Press (1989), etc. It means, in particular, conditions where hybridization occurs at a temperature 5 to 10° C. below the melting temperature (Tm) of a perfect hybrid.

Here, more preferable "stringent conditions" means conditions where hybridization occurs with 90% or more, more preferably 95% or more, and particularly preferably 98% or more sequence homology. Such "stringent conditions" are described in J. Sambrook et al., Molecular Cloning, A Laboratory Manual, Second edition, Cold Spring Harbor Laboratory Press (1989), particularly in Section 11.45 "Conditions for Hybridization of Oligonucleotide Probes", and the conditions may be used here.

In the present invention, homology values between base sequences were calculated using calculation software GENETYX™ Ver. 8 (made by Genetics).

Also, in the present invention, for example, a DNA which hybridizes to a DNA comprising the base sequence of SEQ ID NO: 13 under stringent conditions is preferably a DNA having about 90% or more homology with a DNA comprising a complementary base sequence of SEQ ID NO: 13. The DNA has more preferably about 95% or more, and particularly preferably about 98% or more sequence homology.

In the polymerase chain reaction (PCR) method, the oligonucleotide primer sets shown below may be used to amplify foreign gene sequences which each encode THL, CTF, ADC, or ADH derived from various kinds of living organisms. Examples of such primer sets include the primer set represented by base sequences of SEQ ID NOs: 1 and 2 for amplifying a THL-encoding gene, the primer set represented by base sequences of SEQ ID NOs: 3 and 4 for amplifying a CTF-encoding gene, the primer set represented by base sequences of SEQ ID NOs: 5 and 6 for amplifying an ADC-encoding gene, the primer set represented by base sequences of SEQ ID NOs: 7 and 8 for amplifying an ADH-encoding gene, etc.

In the PCR method, a known PCR device, for example a thermal cycler, may be used. The PCR cycle may be performed according to known techniques. For example, a cycle of denaturation, annealing and extension is repeated usually 10 to 100 times, preferably about 20 to 50 times. Templates used in the PCR to amplify cDNAs of a THL-encoding gene, a CTF-encoding gene, an ADC-encoding gene, and an ADH-encoding gene may be DNAs isolated from a microorganism which exhibits the enzyme activity responsible for the above-mentioned isopropanol-producing pathway. A gene obtained by the PCR method may be transferred into a suitable cloning vector. As the cloning method, commercially available PCR cloning systems, such as pGEM-T easy vector system (made by Promega), TOPO TA-cloning system (made by Invitrogen), Mighty Cloning Kit (made by Takara), etc. may be used. Alternatively, a DNA fragment comprising the corresponding region may be obtained by a hybridization method using, as a template, synthetic primers suitably designed based on a known THL-encoding gene, a known CTF-encoding gene, a known ADC-encoding gene, or a known ADH-encoding gene. An example of such a method will be described in detail in Examples.

Construction of Vector

Subsequently, a cloning vector comprising a gene obtained by the PCR method is transferred into a microorganism, for example, *Escherichia coli* JM109 strain for transformation. The transformed strain is cultured in a culture medium containing suitable antibiotics (for example, ampicillin, chloramphenicol, etc.), and cells are collected from the culture. From the collected cells, plasmid DNA is extracted. The extraction of the plasmid DNA can be performed using a known technique. A commercial plasmid extraction kit may also be used for easy extraction. Examples of the commercial plasmid extraction kit include Qiaquick plasmid purification kit (trade name) made by QIAGEN. By determining the base sequence of this extracted plasmid DNA, the existence of the sequences of a THL-encoding gene, a CTF-encoding gene, an ADC-encoding gene, and an ADH-encoding gene can be confirmed. The base sequence of the DNA can be determined by a known method, for example, the dideoxychain termination method etc. Alternatively, the base sequence can also be determined using a capillary electrophoretic system which utilizes multi-fluorescence technique for detection. Alternatively, the base sequence can also be determined using a DNA sequencer, for example, ABI PRISM 3730×1 DNA Analyzer (made by Applied Biosystem) etc.

The above-mentioned methods can be performed based on conventional methods of genetic engineering experiments. Vectors of various kinds of microorganisms, and methods for transfer and expression of foreign genes are described in many experimental books (for example, Sambrook, J. & Russell, D. W. Molecular Cloning: A Laboratory Manual (3rd Edition) CSHL Press (2001), or Ausubel, F. et al. Current protocols in molecular biology. Green Publishing and Wiley InterScience, New York (1987), etc). Therefore, selection of vectors, and transfer and expression of genes can be performed according to these books.

A wide variety of promoters can suitably be used in the present invention. Such a promoter may be obtained from many known supply sources including yeast, bacteria, and other cell supply sources and may be any base sequence as long as it has a function to start transcription of a target gene in an aerobic bacterium or a facultative anaerobic bacterium. As suitable examples of such a promoter, for example, the lac promoter, the trc promoter, the tac promoter, etc. can be used in *Escherichia coli* and *coryneform* bacteria. The promoter used in the present invention may be modified for change in its regulatory mechanism. The terminator placed downstream of a target gene under a regulatory sequence may also be any base sequence as long as it has a function to terminate transcription of the gene in an aerobic bacterium or a facultative anaerobic bacterium.

Next, a THL-encoding gene, a CTF-encoding gene, an ADC-encoding gene, and an ADH-encoding gene are expressed on a plasmid or a chromosome in an aerobic bacterium or a facultative anaerobic bacterium mentioned above. For example, using a plasmid, these genes are transferred under a regulatory sequence so as to be expressible. Herein, "under a regulatory sequence" means that cooperative work of these genes with, for example, a promoter, an inducer, an operator, a ribosome binding site and a transcription terminator can achieve transcription and translation. A plasmid vector used for such a purpose may be any plasmid vector as long as it comprises a gene responsible for autonomously replicating function in an aerobic bacterium or a facultative anaerobic bacterium. Specific examples of the plasmid vector include, for example, plasmid vectors used for *Escherichia coli* including pUC18, pUC19, pBR322, pET, pCold, pGEX, and derivatives thereof, etc. Examples of the plasmid vector used for coryneform bacteria include pAM330 derived from *Brevibacterium lactofermentum* 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the *Brevibacterium lactofermentum* plasmid pAM330 and the analysis of its genetic information. Nucleic Acids Symp. Ser. 16:265-267 (1985)) ; pHM1519 derived from *Corynebacterium glutamicum* ATCC13058 (Miwa, K. et al., Cryptic plasmids in glutamic acid-producing bacteria. Agric., Biol., Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from *Corynebacterium glutamicum* T250 (JP 57-183799 A; and Katsumata, R. et al., Protoplast transformation of glutamate-producing bacteria with plasmid DNA. J. Bacteriol., 159: 306-311 (1984)), pAG1, pAG3, pAG14 and pAG50 derived from the same (JP 62-166890 A), and pEK0, pEC5 and pEKEx1 derived from the same (Eikmanns, B. J. et al., A family of *Corynebacterium glutamicum/Escherichia coli* shuttle vectors for cloning, controlled gene expression, and promoter probing. Gene, 102:93-98 (1991)) ; derivatives thereof; etc. The examples include yeast plasmids (YEp, YCp, etc.), phage DNA, etc. as well. Any other vector may be used as long as it is capable of replication in a host. The vector preferably comprises a multicloning site which comprises various kinds of restriction enzyme sites inside, or a single restriction enzyme site.

The plasmid vector used for creating a transformed aerobic bacterium or facultative anaerobic bacterium of the present invention, for example in the case where the thl gene, the ctfAB gene and the adc gene derived from *Clostridium aceto-*

*butylicum*, and the adh gene derived from *Clostridium beijerinckii* are used, can be constructed by ligating each of the genes whose base sequences have already been confirmed to a suitable regulatory sequence such as promoters and terminators, and subsequently inserting in a suitable restriction enzyme site of one of the above-mentioned plasmid vectors. Details are described in Examples.

Transformation

The method for transferring a plasmid vector comprising a target gene into an aerobic bacterium or a facultative anaerobic bacterium may be a known method, such as the calcium chloride/rubidium chloride method, the calcium phosphate method, the DEAE-dextran transfection, and the electroporation. Specifically, in the case of *Escherichia coli* for example, the calcium chloride method or the electroporation (for example, Sambrook, J. & Russell, D. W. Molecular Cloning: A Laboratory Manual (3rd Edition) CSHL Press (2001); or Ausubel, F. et al. Current protocols in molecular biology. Green Publishing and Wiley InterScience, New York (1987) etc.), may be used. Also, a method of using *Escherichia coli* JM109 Competent Cells (made by TAKARA SHUZO) may be performed according to the company's protocol. In the case of coryneform bacteria, an electric pulse method may be performed by a known method (Kurusu, Y. et al., Electroporation-transformation system for Coryneform bacteria by auxotrophic complementation., Agric., Biol. Chem. 54:443-447 (1990); and Vertes A. A. et al., Presence of mrr- and mcr-like restriction systems in Coryneform bacteria. Res. Microbiol. 144:181-185 (1993)).

The above methods may be performed based on a conventional method for gene engineering experiments. Information on vectors of various kinds of microorganisms, such as *Escherichia coli* and actinomycetes, and methods for transfer and expression of foreign genes are described in many experimental books (for example, Sambrook, J. & Russell, D. W. Molecular Cloning: A Laboratory Manual, 3rd Edition, CSHL Press, 2001; Hopwood, D. A., Bibb, M. J., Charter, K. F., Bruton, C. J., Kieser, H. M., Lydiate, D. J., Smith, C. P., Ward, J. M., Schrempf, H. Genetic manipulation of *Streptomyces*: A Laboratory manual, The John Innes institute, Norwich, UK, 1985; etc.). Therefore, selection of vectors, and transfer and expression of genes can be performed according to these books.

Specific examples of the transformant of an aerobic bacterium or a facultative anaerobic bacterium created by a method described above include *Escherichia coli* JM109/pCRC201 (deposited under Accession Number FERM BP-10978 in International Patent Organism Depositary, National Institute of Advanced Industrial Science and Technology, Tsukuba Central 6 (1-1-1, Higashi, Tsukuba, Ibaraki, 305-8566 Japan) on Aug. 13, 2007) and *Escherichia coli* JM109/pCRC202 (deposited under Accession Number FERM BP-10979 in International Patent Organism Depositary, National Institute of Advanced Industrial Science and Technology, Tsukuba Central 6 (1-1-1, Higashi, Tsukuba, Ibaraki, 305-8566 Japan) on Aug. 13, 2007).

In the same manner as described above, it is also possible to create a transformant of *Corynebacterium* capable of producing isopropanol.

For improving production of isopropanol, the transformant of the present invention may include genetic modification which leads to one or more characteristics selected from the group consisting of increased flow in glycolytic system, increased resistance to isopropanol osmotic pressure or organic acids, and reduced production of by-products (carbon-containing molecules other than the target product). Such genetic modification can be introduced, in particular, by overexpression of a foreign gene and/or inactivation of an endogenous gene, classic mutagenesis, screening and/or target mutant sorting, etc.

A transformant may be mutated by artificial mutagenesis with the use of ultraviolet, X-rays, or an agent. Any mutant obtained in such a way may be used as a transformed microorganism of the present invention, as long as it is capable of producing isopropanol, achieving the object of the present invention.

The thus created transformant of an aerobic bacterium or a facultative anaerobic bacterium of the present invention (hereinafter referred to simply as the transformant) may be cultured using a culture medium commonly used for culture of microorganisms. The culture medium may be a natural medium or a synthetic medium containing a carbon source, a nitrogen source, inorganic salts, other nutritional substances, etc.

Examples of the carbon source include, for example, carbohydrates and sugar alcohols such as glucose, fructose, sucrose, mannose, maltose, mannitol, xylose, galactose, starch, molasses, sorbitol and glycerol; organic acids such as acetic acid, citric acid, lactic acid, fumaric acid, maleic acid and gluconic acid; and alcohols such as ethanol. Hydrocarbons, such as normal paraffin, etc. may be used if desired. These carbon sources may be used alone or as a mixture of two or more thereof. The concentration of these carbon sources in a culture medium is usually about 0.1 to 10% by weight and preferably about 0.5 to 5% by weight.

Examples of the nitrogen source include nitrogen compounds, for example, inorganic or organic ammonium compounds such as ammonium chloride, ammonium sulfate, ammonium nitrate, and ammonium acetate; urea; aqueous ammonia; sodium nitrate; and potassium nitrate, but the nitrogen source is not limited thereto. Nitrogen-containing organic compounds such as corn steep liquor, meat extract, peptone, N-Z-amine, protein hydrolysate, amino acid, etc. may be used. These nitrogen sources may be used alone or as a mixture of two or more thereof. The concentration of these nitrogen sources in a culture medium varies depending on the kind of the nitrogen compound, but is usually about 0.1 to 10% by weight and preferably about 0.5 to 5% by weight.

Examples of the inorganic salts include, for example, potassium dihydrogen phosphate, dipotassium hydrogenphosphate, magnesium sulfate, sodium chloride, iron (II) nitrate, manganese sulfate, zinc sulfate, cobalt sulfate, and calcium carbonate. These inorganic salts may be used alone or as a mixture of two or more thereof. The concentration of these inorganic salts in a culture medium varies depending on the kind of the inorganic salt, but is usually about 0.01 to 1.0% by weight and preferably about 0.05 to 0.5% by weight.

Examples of the nutritional substances include, for example, meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of these nutritional substances in a culture medium varies depending on the kind of the nutritional substance, but is usually about 0.1 to 10% by weight and preferably about 0.5 to 5% by weight. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of preferable microbial culture medium include LB (Luria-Bertani) medium, SD8 medium, NZYM medium, TB (Terrific Broth) medium, SOB medium, 2×YT medium, M9 medium, etc. for *Escherichia coli*; and A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc. for coryneform bacteria.

The culture temperature is about 15 to 45° C., preferably about 25 to 40° C., and the culture period is about 1 to 7 days, preferably about 1 to 3 days.

Subsequently, cultured bacterial cells of the transformant are collected. The method for collecting and isolating cultured bacterial cells from the culture obtained as described above is not particularly limited, and any known method, such as centrifugal separation and membrane separation, may be used.

The collected bacterial cells may be subjected to some treatment and then the resulting treated bacterial cells may be used in the next step. As long as the cultured bacterial cells have undergone some treatment, they can be used as the treated bacterial cells. Examples of the treated bacterial cells include immobilized bacterial cells obtained by treatment with, for example, acrylamide, carrageenan, or the like.

(II) Method for Producing Isopropanol

The cultured bacterial cells of the transformant collected and isolated from the culture or treated bacterial cells thereof obtained as described above are subjected to isopropanol-producing reaction in a reaction culture medium under aerobic or anaerobic conditions. The method for producing isopropanol comprising a step of culturing the above-mentioned transformant in a culture medium containing saccharides (reaction culture medium) and a step of collecting isopropanol from the culture is also comprised in the present invention.

The method for producing isopropanol may be any of a batch method, a feeding method, and a continuous method.

The reaction culture medium (reaction mixture) may be any culture medium as long as it contains an organic carbon source (for example, saccharides etc.) as a raw material of isopropanol. The organic carbon source may be any substance as long as the transformant of the present invention can utilize the substance for a biochemical reaction.

Specific examples of saccharides include monosaccharides such as glucose, xylose, arabinose, galactose, fructose and mannose; disaccharides such as cellobiose, sucrose, lactose and maltose; poly saccharides such as dextrin and soluble starch; etc. In particular, monosaccharides such as C6 sugars and C5 sugars are preferred. However, in some cases, coryneform bacteria cannot assimilate C5 monosaccharides such as xylose, arabinose, etc. In such cases, a function to assimilate those monosaccharides should be given to the bacteria. In the present invention, a mixture of two or more kinds of saccharides may also be used.

More preferably, a reaction culture medium used for a reaction for producing an organic compound contains ingredients necessary for the transformant or treated transformant to maintain its metabolic functions, that is, carbon sources such as various saccharides; nitrogen sources necessary for protein synthesis; and others including salts of phosphorus, potassium, sodium, etc. and salts of trace metals such as iron, manganese and calcium. The amounts of such ingredients may be suitably determined depending on the necessary reaction time, the target organic compound, or the transformant to be used. Depending on the transformant to be used, addition of certain vitamins may be preferred. The carbon source, the nitrogen source, the inorganic salts, the vitamin, and the trace metal salt to be used may be known ingredients, for example, those illustrated in the step of propagation and culturing.

Usually, preferred pH of the reaction culture medium is about 6 to 8.

The reaction of the transformant or treated bacterial cells thereof with saccharides is preferably performed under temperature conditions in which the transformant of the present invention or treated bacterial cells thereof can work. The temperature may be suitably determined depending on the transformant or treated bacterial cells thereof, etc., and is usually about 25 to 35° C.

Finally, isopropanol produced in a reaction culture medium as described above is collected. A known method used in the field of bioprocess may be used. Examples of such a known method for collecting produced isopropanol include distillation, membrane permeation method, organic solvent extraction method, etc. The method for separation, purification and collection may be suitably determined depending on the composition of the reaction mixture, by-products, etc.

The present invention further provides a recombinant isopropanol-producing transformant with remarkably improved capability to produce isopropanol from saccharides etc. by a reaction under the conditions described above.

EXAMPLES

Hereinafter, the present invention will be illustrated in more detail by Examples, but is not limited thereto.

Example 1

Creation of *Escherichia coli* JM109/pCRC201 and *Escherichia coli* JM109/pCRC202

(1) Cloning of a Group of Isopropanol-Producing Genes

The isopropanol biosynthesis pathway (from acetyl CoA to isopropanol) in *Clostridium* bacteria consists of 4 steps involving 4 enzymes i.e., acetyl-CoA acetyltransferase, acetoacetyl CoA:acetate CoA-transferase, acetoacetate decarboxylase, and isopropanol dehydrogenase. Respective genes which encode these 4 enzymes were amplified by the PCR method as described below.

Using chromosomal and plasmid DNAs of *Clostridium acetobutylicum* ATCC 824 (ATCC 824D-5) obtained from American Type Culture Collection (ATCC) as templates, and using primers 1 and 2 (SEQ ID NOs: 1 and 2), primers 3 and 4 (SEQ ID NOs: 3 and 4), and primers 5 and 6 (SEQ ID NOs: 5 and 6), an acetyl-CoA acetyltransferase gene (thl), an acetoacetyl CoA:acetate CoA-transferase gene (ctfAB), and an acetoacetate decarboxylase gene (adc) were respectively amplified by PCR. PCR was performed using GeneAmp PCR System 9700 (made by Applied Biosystems) under the conditions of PCR Reaction 1 (30 cycles of 94° C. for 30 seconds, 58° C. for 30 seconds, and 72° C. for 1.5 minutes; template DNA 10 ng; reaction mixture: dNTP 0.2 mM, PrimeSTAR DNA polymerase (made by TAKARA) 2U, 5× PrimeSTAR buffer 6 and each primer 0.2 µM; final volume 30 µL). Using 3 µL of the above amplified reaction mixture, 0.8% agarose gel electrophoresis was performed. In the case of the thl gene, the ctfAB gene, and the adc gene, about 1.2-kb, about 1.3-kb, and about 0.7-kb DNA fragments were respectively detected. The amplified DNA fragments were purified using MinElute PCR Purification Kit (made by QIAGEN).

*Clostridium* beijerinckii NRRL B593 was cultured in the reinforced Clostridial medium (made by Difco) under anaerobic conditions at 30° C. After 16-hour culture, 5 mL of the culture medium was centrifuged (high speed refrigerated micro centrifuge MX-301 made by TOMY SEIKO, 5,000 rpm, 10 minutes), and precipitated bacterial cells were subjected to extraction of chromosomal DNA. The extraction of chromosomal DNA was performed in the following procedure. That is, the bacterial cells were suspended in 0.3 mL of TESS buffer (25 mM Tris-HCl (pH 8.0), 5 mM EDTA, 50 mM NaCl, 25% Sucrose). To the suspension, 0.3 mL of lysozyme solution (100 mg/mL) was added, and the mixture was allowed to stand on ice for 30 minutes. Subsequently, 0.6 mL of 2% sodium dodecyl sulfate solution and 40 μL of 10 mg/mL Proteinase K solution (made by Sigma) were added, and the mixture was kept at 50° C. After 2 hours, an equivalent amount of phenol:chloroform mixture was added, and the mixture was stirred at room temperature for 10 minutes. This solution was centrifuged (12,000 rpm, 10 minutes), and the supernatant was collected. To this, 120 μL of 3M sodium acetate solution and 720 μL of isopropanol were added. After mixing this well, centrifugation (15,000 rpm, 10 minutes) was performed to precipitate chromosomal DNA. The supernatant was removed, and separated chromosomal DNA was washed with 1 mL of 70% ethanol. Centrifugation (15,000 rpm, 10 minutes) was performed again to collect chromosomal DNA. The collected chromosomal DNA was left stand at room temperature for 10 minutes to be dried, and then dissolved in 100 μL of TE (10 mM Tris-HCl, 0.5 mM EDTA). Using the chromosomal DNA of Clostridium beijerinckii NRRL B593 as a template, and using primers 7 and 8 (SEQ ID NOs: 7 and 8), an isopropanol dehydrogenase gene (adh) was amplified under the conditions of the above-mentioned PCR Reaction 1. Using 3 μL of the above amplified reaction mixture, 0.8% agarose gel electrophoresis was performed, and an about 1.1-kb DNA fragment comprising the adh gene was detected. The amplified DNA fragment was purified using MinElute PCR Purification Kit.

In order to obtain a gene expression promoter (tac promoter), using pKK223-3 (made by Pharmacia) as a template, and using primers 9 and 10 (SEQ ID NOs: 9 and 10), an about 0.2-kb DNA fragment comprising a tac promoter was amplified under the conditions of the above-mentioned PCR Reaction 1. After the end of the reaction, the amplified DNA fragment was purified using MinElute PCR Purification Kit (made by QIAGEN).

Ligation of the tac promoter with the about 1.3-kb DNA fragment comprising the ctfAB gene, the about 0.7-kb DNA fragment comprising the adc gene, or the about 1.1-kb DNA fragment comprising the adh gene, obtained in the above-mentioned PCR Reaction 1, was performed in the following procedure. That is, any of the above three kinds of DNA fragments, and the DNA fragment comprising the tac promoter were mixed in amounts of about 100 ng each. To this, 0.2 mM of dNTP, 2 U of PrimeSTAR DNA polymerase (made by TAKARA), and 6 μL of 5× PrimeSTAR buffer were added and mixed so that the final volume might be 30 μL. This reaction mixture was reacted using GeneAmp PCR System 9700 under the conditions of PCR Reaction 2 (30 cycles of 94° C. for 30 seconds, 52° C. for 30 seconds, and 72° C. for 1.5 minutes). After the end of the reaction, in order to obtain a DNA fragment in which the tac promoter was ligated to the ctfAB, adc or adh gene, 0.5 μL of the reaction mixture as a template was amplified by PCR under the conditions of the above-mentioned PCR Reaction 1 using primers 4 and 9 (SEQ ID NOs: 4 and 9), primers 6 and 11 (SEQ ID NOs: 6 and 11), or primers 8 and 12 (SEQ ID NOs: 8 and 12). Using 3 μL of the above amplified reaction mixture, 0.8% agarose gel electrophoresis was performed. As a result, an about 1.5-kb DNA fragment comprising the ctfAB gene ligated to the tac promoter (Ptac-ctfAB), an about 0.9-kb DNA fragment comprising the adc gene ligated to the tac promoter (Ptac-adc), and an about 1.3-kb DNA fragment comprising the adh gene ligated to the tac promoter (Ptac-adh) were detected. Each DNA fragment was separated by agarose gel electrophoresis and then collected from the gel using MinElute Gel Extraction Kit (made by QIAGEN).

The above-mentioned about 1.2-kb thl DNA fragment without any ligated tac promoter, about 1.5-kb DNA fragment comprising the Ptac-ctfAB, about 0.9-kb DNA fragment comprising the Ptac-adc, or about 1.3-kb DNA fragment comprising the Ptac-adh was ligated to a pGEM-T vector (made by Promega) according to the instruction manual, and Escherichia coli JM109 was transformed by the calcium chloride method (Journal of Molecular Biology, 53, and 159 (1970)). The resultant solution was applied to a LB agar medium (10 g of poly peptone, 5 g of yeast extract, 5 g of NaCl, and 15 g of agar were dissolved in 1 L of distilled water) containing 50 μg/mL of ampicillin. In each case, growing strains on the culture medium were subjected to liquid culture in the usual manner. Plasmid DNA was extracted from the culture medium and cut with the use of restriction enzymes to confirm the inserted fragment. Furthermore, sequencing of the inserted fragment was performed to confirm that the target DNA sequence had been constructed. Plasmids comprising the thl gene (SEQ ID NO: 13), the ctfAB gene (SEQ ID NO: 14), the adc gene (SEQ ID NO: 15) and the adh gene (SEQ ID NO: 16) were named pGEM-thl, pGEM-Ptac-ctfAB, pGEM-Ptac-adc, and pGEM-Ptac-adh, respectively. ABI PRISM3100 (made by Applied Biosystems) as a DNA sequencer, and ABI PRISM Cycle Sequencing Kit (made by Applied Biosystems) for sequence reaction were used. The plasmids pGEM-thl, pGEM-Ptac-ctfAB, pGEM-Ptac-adc and pGEM-Ptac-adh thus prepared were cut with the use of restriction enzymes EcoRI and BamHI, BamHI and SphI, SphI and SmaI, and SmaI and HindIII, respectively, and then each of them was separated by agarose gel electrophoresis. Using MinElute Gel Extraction Kit (made by QIAGEN) for collection from the gel, an about 1.2-kb EcoRI-BamHI DNA fragment comprising the thl gene without any ligated tac promoter, an about 1.5-kb BamHI-SphI DNA fragment comprising the Ptac-ctfAB gene comprising the tac promoter, an about 0.9-kb SphI-SmaI DNA fragment comprising the Ptac-adc gene comprising the tac promoter, and an about 1.3-kb SmaI-HindIII DNA fragment comprising the Ptac-adh gene comprising the tac promoter were obtained.

(2) Construction of Expression Vector pCRC200

Preparation of gene expression vector pCRC200 was performed in the following procedure. That is, using pKK223-3 as a template, and using primers 13 and 14 (SEQ ID NOs: 17 and 18), a DNA fragment comprising the tac promoter-rrnB terminator region was amplified under the conditions of the PCR Reaction 1 in the above (1). Next, Escherichia coli vector pCRB1 (Nakata, K. et al. Vectors for the genetics engineering of corynebacteria; in Saha, B. C. (ed.): Fermentation Biotechnology, ACS Symposium Series 862. Washington, American Chemical Society, 175-191 (2003)) was digested by EcoRI, and the DNA terminus was smoothed using DNA Blunting Kit (made by TAKARA) according to the instruction manual, for self ligation. Next, the obtained plasmid was digested by HindIII, and the DNA terminus was smoothed using DNA Blunting Kit in the same manner for self ligation. The plasmid thus obtained was digested by SacI and SphI. In the same manner, the DNA fragment comprising the tac promoter-rrnB terminator region was digested by SacI and SphI. Subsequently, using DNA ligation kit (made by TAKARA), these two DNA fragments were ligated according to the instruction manual. The reaction mixture was used to transform *Escherichia coli* JM109 by the calcium chloride method. The resultant solution was applied to a LB agar medium (10 g of poly peptone, 5 g of yeast extract, 5 g of NaCl, and 15 g of agar were dissolved in 1 L of distilled water) containing 50 μg/mL of chloramphenicol. A growing strain on the culture medium was subjected to liquid culture in the usual manner. Plasmid DNA was extracted from the culture medium and cut with the use of restriction enzymes to confirm the inserted fragment. A plasmid comprising the target gene fragments was named pCRC200 (SEQ ID NO: 19).

(3) Construction of expression plasmids pCRC201 and pCRC202, and creation of *Escherichia coli* JM109/pCRC201 and *Escherichia coli* JM109/pCRC202

The DNA fragments obtained in the above (1), that is, the about 1.2-kb EcoRI-BamHI DNA fragment comprising the thl gene without any ligated tac promoter, the about 1.5-kb BamHI-SphI DNA fragment comprising the Ptac-ctfAB gene comprising the tac promoter, the about 0.9-kb SphI-SmaI DNA fragment comprising the Ptac-adc gene comprising the tac promoter, and the about 1.3-kb SmaI-HindIII DNA fragment comprising the Ptac-adh gene comprising the tac promoter in amounts of 100 ng each, and 10 ng of pKK223-3 digested by EcoRI and HindIII beforehand were all mixed, and ligation was performed using DNA ligation kit. This reaction ligates a tac promoter to the thl gene also. The pKK223-3 has a replication origin derived from pBR322, whose copy number in *Escherichia coli* is 15 to 20 (Sambrook, J. et al. Molecular cloning: a laboratory manual, 2nd edn. Cold Spring Harbor, N.Y.: Cold Spring Harbor Laboratory Press (1989)). *Escherichia coli* JM109 was transformed by the calcium chloride method using this ligation liquid, and by selecting an *Escherichia coli* strain carrying a plasmid DNA comprising the target gene fragments, plasmid pCRC201 was obtained (FIG. 1, SEQ ID NO: 20). The *Escherichia coli* JM109/pCRC201 transformant carrying this plasmid was deposited in International Patent Organism Depositary, National Institute of Advanced Industrial Science and Technology, Tsukuba Central 6 (1-1-1, Higashi, Tsukuba, Ibaraki, 305-8566 Japan) under Accession Number FERM BP-10978 on Aug. 13, 2007.

Figure 2:
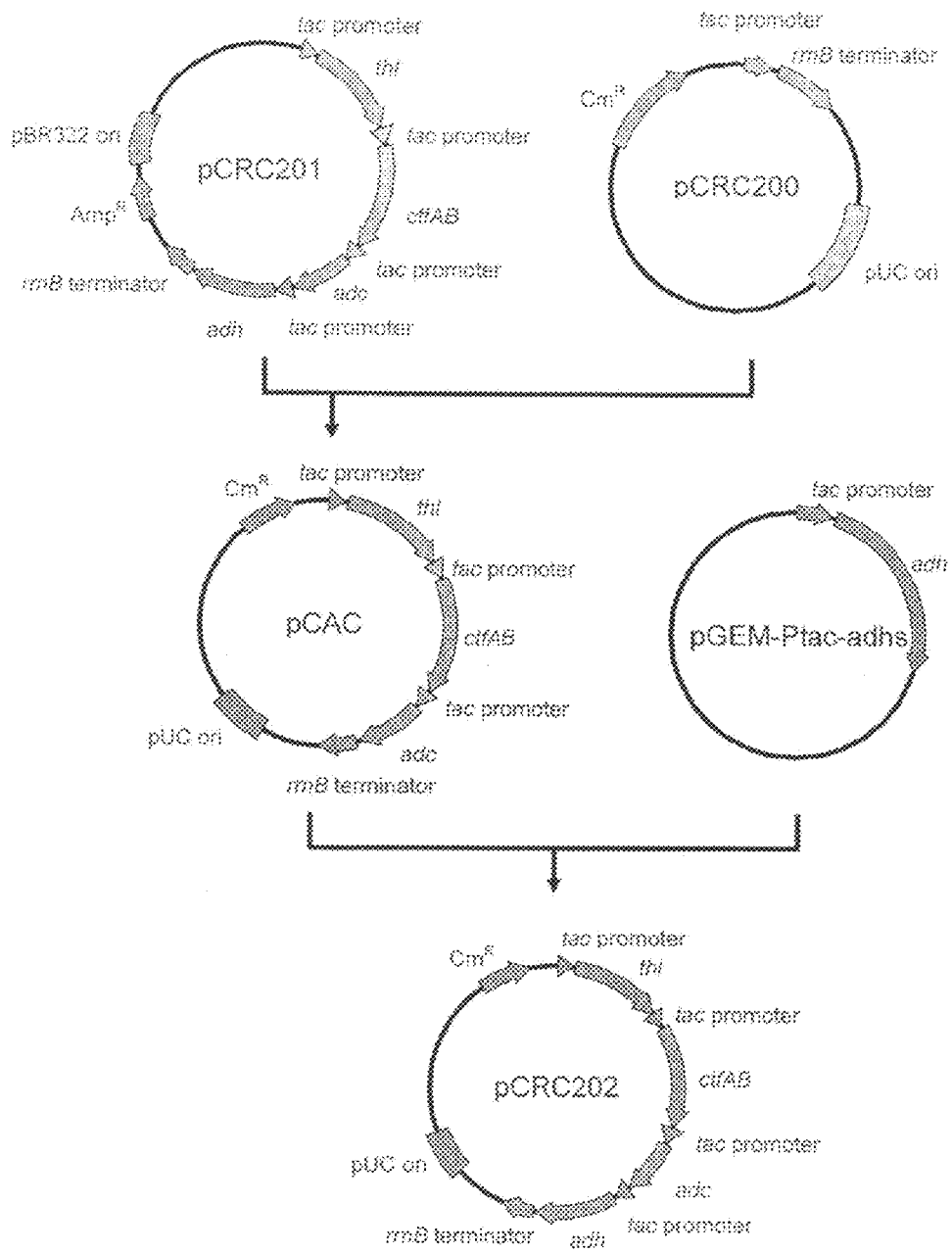
FIG. 2 shows a method for preparing the plasmid pCRC202 in Example 1 (3).

The above plasmid pCRC201 was digested by EcoRI and SmaI to prepare an about 3.6-kb EcoRI-SmaI DNA fragment comprising the thl gene, the Ptac-ctfAB gene, and the Ptac-adc gene. Next, the obtained DNA fragment was ligated to pCRC200, which was constructed in the above (2) and digested by EcoRI and SmaI beforehand, to give a plasmid pCAC. By this operation, the thl gene is also ligated to the tac promoter. The pCRC200 has a replication origin derived from pUC vector, whose copy number in *Escherichia coli* is 500 to 700 (Sambrook, J. et al. Molecular cloning: a laboratory manual, 2nd edn. Cold Spring Harbor, N.Y.: Cold Spring Harbor Laboratory Press (1989)). Next, using a plasmid, pGEM-Ptac-adh (SEQ ID NO: 16), as a template, and using primers 12 and 15 (SEQ ID NO: 21), a Ptac-adh gene to which a SalI recognition sequence was added was amplified under the conditions of PCR Reaction 1 in the above (1). The resultant reaction mixture was purified using MinElute PCR Purification Kit (made by QIAGEN), and the DNA fragment was ligated to a pGEM-T vector (made by Promega) according to the instruction manual to give a plasmid pGEM-Ptac-adhs. The plasmid thus prepared was digested by SmaI and SalI to prepare an about 1.3-kb DNA fragment comprising the Ptac-adh gene. This DNA fragment was ligated to pCAC digested by SmaI and SalI beforehand, to give a plasmid pCRC202 (FIG. 2, SEQ ID NO: 22). This plasmid was transferred into *Escherichia coli* JM109 to give *Escherichia coli* JM109/pCRC202 transformant. This transformant strain was deposited in International Patent Organism Depositary, National Institute of Advanced Industrial Science and Technology, Tsukuba Central 6 (1-1-1, Higashi, Tsukuba, Ibaraki, 305-8566 Japan) under Accession Number FERM BP-10979 on Aug. 13, 2007.

Example 2

Production of Isopropanol by *Escherichia coli* JM109/pCRC201 Transformant

*Escherichia coli* JM109/pCRC201 was cultured with shaking in a LB liquid medium (10 g of poly peptone, 5 g of yeast extract and 5 g of NaCl were dissolved in 1 L of distilled water) containing 200 μg/mL of ampicillin at 37° C. for about 16 hours. 500 μL of this culture medium was inoculated in 50 mL of SD8 medium (1 L of aqueous solution containing 7 g of $NH_4Cl$, 7.5 g of $KH_2PO_4$, 7.5 g of $Na_2HPO_4$, 0.85 g of $K_2SO_4$, 0.17 g of $MgSO_4 7H_2O$, 10 g of yeast extract, 20 g of glucose and 0.8 mL of trace elements (40 g of $FeSO_4 7H_2O$, 10 g of $MnSO_4 H_2O$, 28.3 g of $Al_2(SO_4)_3$, 4 g of $CoCl6H_2O$, 2 g of $ZnSO_4 7H_2O$, 2 g of $Na_2MoO_4 2H_2O$, 1 g of $CuCl_2 2H_2O$ and 0.5 g of $H_3BO_4$ dissolved in 1 L of 5M HCl)) containing 200 μg/mL of ampicillin. Culture was performed with shaking using a 500-mL baffle flask at 37° C. Glucose was added to the culture medium as needed. Isopropanol in the culture medium was analyzed using gas chromatograph GC-14B (made by Shimadzu) equipped with Sunpak-A 50/80 Thermon-1000 (2.1 m×3.2 mm I.D., made by Shinwa Chemical). Analysis was performed under conditions of 35 mL/min nitrogen, 60 kPa hydrogen, 60 kPa air, the injection temperature and FID detector temperature of 200° C., and the column temperature was controlled so as to be kept at 130° C. for 13 minutes and then raised up to 160° C. at a heating rate of 10° C./min. After predetermined time of culture, the culture medium was centrifuged (15,000 rpm for 5 minutes), and obtained supernatant was analyzed for isopropanol production by gas chromatography.

At 24 hours and 48 hours after the start of culturing *Escherichia coli* JM109/pCRC201, the reaction mixture was centrifuged (15,000×g at 4° C. for 10 minutes) and analyzed for isopropanol production by gas chromatography. The results show that isopropanol production at 24 hours was 14 mM and at 48 hours was 11 mM.

Comparative Example 1

In the same manner and under the same conditions as in Example 2 except that *Escherichia coli* JM109 was used instead of *Escherichia coli* JM109/pCRC201 and that ampicillin was not added to LB medium and SD8 medium, an experiment of isopropanol production was conducted.

As a result, *Escherichia coli* JM109 did not produce isopropanol. A comparison with the results of Example 2 shows that *Escherichia coli* JM109/pCRC201 was capable of producing isopropanol.

Example 3

Production of Isopropanol by *Escherichia coli* JM109/pCRC202 Transformant

In the same manner and under the same conditions as in the Example 2 except that *Escherichia coli* JM109/pCRC202 was used instead of *Escherichia coli* JM109/pCRC201, an experiment of isopropanol production was conducted.

At 24 hours and 48 hours after the start of culturing *Escherichia coli* JM109/pCRC202, the reaction mixture was centrifuged (15,000×g at 4° C. for 10 minutes) and analyzed for isopropanol production by gas chromatography. The results show that isopropanol production at 24 hours was 75 mM and at 48 hours was 162 mM.

A comparison with the results of JM109/pCRC201 in Example 2 shows that *Escherichia coli* JM109/pCRC202 has higher ability to produce isopropanol.

INDUSTRIAL APPLICABILITY

The transformant of the present invention is useful because it is capable of extremely efficient production of isopropanol from saccharides.

The present invention enables efficient isopropanol production from renewable resources and construction of a new process for industrially producing isopropanol without depending on petroleum resources.

The invention claimed is:

1. A transformant capable of producing isopropanol, which is constructed by transferring the following genes (a) to (d) into *Escherichia coli* JM 109:
   (a) DNA comprising the base sequence of SEQ ID NO: 13, or a DNA having 95% or more sequence identity to SEQ ID NO: 13 and encoding an enzyme having acetyl-CoA acetyltransferase activity;
   (b) DNA comprising the base sequence of SEQ ID NO: 14, or a DNA having 95% or more sequence identity to SEQ ID NO: 14 and encoding an enzyme having acetoacetyl CoA:acetate CoA-transferase activity;
   (c) DNA comprising the base sequence of SEQ ID NO: 15, or a DNA having 95% or more sequence identity to SEQ ID NO: 15 and encoding an enzyme having acetoacetate decarboxylase activity; and
   (d) DNA comprising the base sequence of SEQ ID NO: 16, or a DNA having 95% or more sequence identity to SEQ ID NO: 16 and encoding an enzyme having isopropanol dehydrogenase activity, wherein the DNAs of (a), (b) and (c) are derived from *Clostridium acetobutylicum*, and the DNA of (d) is derived from *Clostridium beiierinckii*.

2. The transformant according to claim 1, which is *Escherichia coli* JM 109/pCRC201 (Accession Number: FERM BP-10978) or *Escherichia coli* JM 109/pCRC202 (Accession Number FERM BP-10979).

3. A method for producing isopropanol, which comprises a step of culturing the transformant according to claim 1 in a culture medium containing saccharides, and a step of collecting isopropanol from a culture thereof.

4. A method for producing isopropanol, which comprises a step of culturing the transformant according to claim 2 in a culture medium containing saccharides, and a step of collecting isopropanol from a culture thereof.

* * * * *

UNITED STATES PATENT AND TRADEMARK OFFICE
CERTIFICATE OF CORRECTION

PATENT NO.           : 8,426,172 B2
APPLICATION NO.      : 12/733366
DATED                : April 23, 2013
INVENTOR(S)          : Hideaki Yukawa It is certified that error appears in the above-identified patent and that said Letters Patent is hereby corrected as shown below:

Title Page,

In Item (73) Assignee, please amend the following:

Research Institute of ~~Innovation~~Innovative Technology for the Earth

Signed and Sealed this
Ninth Day of July, 2013

Teresa Stanek Rea
*Acting Director of the United States Patent and Trademark Office*

```
                        SEQUENCE LISTING

<160> NUMBER OF SEQ ID NOS: 22

<210> SEQ ID NO 1
  <211> LENGTH: 44
  <212> TYPE: DNA
  <213> ORGANISM: Artificial sequence
  <220> FEATURE:
  <223> OTHER INFORMATION: Primer for PCR

<400> SEQUENCE: 1
cgaattcaaa ggaggagtgt gttgatgaaa gaagttgtaa tagc              44

<210> SEQ ID NO 2
  <211> LENGTH: 25
  <212> TYPE: DNA
  <213> ORGANISM: Artificial sequence
  <220> FEATURE:
  <223> OTHER INFORMATION: Primer

<400> SEQUENCE: 2
ggatccctag cacttttcta gcaat                                   25

<210> SEQ ID NO 3
  <211> LENGTH: 52
  <212> TYPE: DNA
  <213> ORGANISM: Artificial sequence
  <220> FEATURE:
  <223> OTHER INFORMATION: Primer

<400> SEQUENCE: 3
ttcacacagg aaacaaagga ggagtgtgtt gatgaactct aaaataatta ga     52

<210> SEQ ID NO 4
  <211> LENGTH: 26
  <212> TYPE: DNA
  <213> ORGANISM: Artificial sequence
  <220> FEATURE:
  <223> OTHER INFORMATION: Primer

<400> SEQUENCE: 4
gcatgctaaa cagccatggg tctaag                                  26

<210> SEQ ID NO 5
  <211> LENGTH: 54
  <212> TYPE: DNA
  <213> ORGANISM: Artificial sequence
  <220> FEATURE:
  <223> OTHER INFORMATION: Primer

<400> SEQUENCE: 5
ttcacacagg aaacaaagga ggagtgtgtt gatgttaaag gatgaagtaa ttaa   54

<210> SEQ ID NO 6
  <211> LENGTH: 30
  <212> TYPE: DNA
```

```
<213> ORGANISM: Artificial sequence
<220> FEATURE:
<223> OTHER INFORMATION: Primer

<400> SEQUENCE: 6
cccgggttac ttaagataat catatataac                                            30

<210> SEQ ID NO 7
<211> LENGTH: 52
<212> TYPE: DNA
<213> ORGANISM: Artificial sequence
<220> FEATURE:
<223> OTHER INFORMATION: Primer

<400> SEQUENCE: 7
ttcacacagg aaacaaagga ggagtgtgtt gatgaaaggt tttgcaatgc ta                   52

<210> SEQ ID NO 8
<211> LENGTH: 28
<212> TYPE: DNA
<213> ORGANISM: Artificial sequence
<220> FEATURE:
<223> OTHER INFORMATION: Primer

<400> SEQUENCE: 8
aagcttttat aatataacta ctgcttta                                              28

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
ggatccccat cggaagctgt gg                                                    22

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
tgtttcctgt gtgaaattg                                                        19

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gcatgccatc ggaagctgtg g                                                     21

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
cccgggccat cggaagctgt gg                                                    22
```

<210> SEQ ID NO 13
<211> LENGTH: 1209
<212> TYPE: DNA
<213> ORGANISM: Clostridium acetobutylicum

<400> SEQUENCE: 13

| | | | | | |
|---|---|---|---|---|---|
| cgaattcaaa | ggaggagtgt | gttgatgaaa | gaagttgtaa | tagctagtgc | agtaagaaca | 60 |
| gcgattggat | cttatggaaa | gtctcttaag | gatgtaccag | cagtagattt | aggagctaca | 120 |
| gctataaagg | aagcagttaa | aaaagcagga | ataaaaccag | aggatgttaa | tgaagtcatt | 180 |
| ttaggaaatg | ttcttcaagc | aggtttagga | cagaatccaa | caagacaggc | atcttttaaa | 240 |
| gcaggattac | cagttgaaat | tccagctatg | actattaata | aggtttgtgg | ttcaggactt | 300 |
| agaacagtta | gctagcagc | acaaattata | aagcaggag | atgctgacgt | aataatagca | 360 |
| ggtggtatgg | aaaatatgtc | tagagctcct | tacttagcga | ataacgctag | atggggatat | 420 |
| agaatgggaa | acgctaaatt | tgttgatgaa | atgatcactg | acggattgtg | ggatgcattt | 480 |
| aatgattacc | acatgggaat | aacagcagaa | acatagctg | agagatggaa | catttcaaga | 540 |
| gaagaacaag | atgagtttgc | tcttgcatca | caaaaaaag | ctgaagaagc | tataaaatca | 600 |
| ggtcaattta | aagatgaaat | agttcctgta | gtaattaaag | gcagaaaggg | agaaactgta | 660 |
| gttgatacag | atgagcaccc | tagatttgga | tcaactatag | aaggacttgc | aaaattaaaa | 720 |
| cctgccttca | aaaagatgg | aacagttaca | gctggtaatg | catcaggatt | aaatgactgt | 780 |
| gcagcagtac | ttgtaatcat | gagtgcagaa | aaagctaaag | agcttggagt | aaaaccactt | 840 |
| gctaagatag | tttcttatgg | ttcagcagga | gttgacccag | caataatggg | atatggacct | 900 |
| ttctatgcaa | caaaagcagc | tattgaaaaa | gcaggttgga | cagttgatga | attagattta | 960 |
| atagaatcaa | atgaagcttt | tgcagctcaa | agtttagcag | tagcaaaaga | tttaaaattt | 1020 |
| gatatgaata | agtaaatgt | aaatggagga | gctattgccc | ttggtcatcc | aattggagca | 1080 |
| tcaggtgcaa | gaatactcgt | tactcttgta | cacgcaatgc | aaaaaagaga | tgcaaaaaaa | 1140 |
| ggcttagcaa | ctttatgtat | aggtggcgga | caaggaacag | caatattgct | agaaaagtgc | 1200 |
| tagggatcc | | | | | 1209 |

<210> SEQ ID NO 14
<211> LENGTH: 1557
<212> TYPE: DNA
<213> ORGANISM: Clostridium acetobutylicum

<400> SEQUENCE: 14

| | | | | | |
|---|---|---|---|---|---|
| ggatccccat | cggaagctgt | ggtatggctg | tgcaggtcgt | aaatcactgc | ataattcgtg | 60 |
| tcgctcaagg | cgcactcccg | ttctggataa | tgttttttgc | gccgacatca | taacggttct | 120 |
| ggcaaatatt | ctgaaatgag | ctgttgacaa | ttaatcatcg | gctcgtataa | tgtgtggaat | 180 |
| tgtgagcgga | taacaattc | acacaggaaa | caaggaggag | gtgtgttgat | gaactctaaa | 240 |
| ataattagat | ttgaaaattt | aaggtcattc | tttaaagatg | ggatgacaat | tatgattgga | 300 |
| ggttttttaa | actgtggcac | tccaaccaaa | ttaattgatt | ttttagttaa | tttaaatata | 360 |
| aagaatttaa | cgattataag | taatgataca | tgttatccta | atacaggtat | tggtaagtta | 420 |
| atatcaaata | atcaagtaaa | aaagcttatt | gcttcatata | taggcagcaa | cccagatact | 480 |
| ggcaaaaaac | ttttttaataa | tgaacttgaa | gtagagctct | ctccccaagg | aactctagtg | 540 |
| gaaagaatac | gtgcaggcgg | atctggctta | ggtggtgtac | taactaaaac | aggtttagga | 600 |
| actttgattg | aaaaaggaaa | gaaaaaaata | tctataaatg | gaacggaata | tttgttagag | 660 |

```
ctacctctta cagccgatgt agcattaatt aaaggtagta ttgtagatga ggccggaaac    720
accttctata aaggtactac taaaaacttt aatccctata tggcaatggc agctaaaacc    780
gtaatagttg aagctgaaaa tttagttagc tgtgaaaaac tagaaaagga aaaagcaatg    840
accccccggag ttcttataaa ttatatagta aaggagcctg cataaaatga ttaatgataa    900
aaacctagcg aaagaaataa tagccaaaag agttgcaaga gaattaaaaa atggtcaact    960
tgtaaactta ggtgtaggtc ttcctaccat ggttgcagat tatataccaa aaaatttcaa   1020
aattactttc caatcagaaa acggaatagt tggaatgggc gctagtccta aaataaatga   1080
ggcagataaa gatgtagtaa atgcaggagg agactataca acagtacttc ctgacggcac   1140
atttttcgat agctcagttt cgttttcact aatccgtggt ggtcacgtag atgttactgt   1200
tttaggggct ctccaggtag atgaaaaggg taatatagcc aattggattg ttcctggaaa   1260
aatgctctct ggtatgggtg agctatggga tttagtaaat ggagctaaga agtaataat   1320
tgcaatgaga catacaaata aaggtcaacc taaaatttta aaaaaatgta cacttcccct   1380
cacggcaaag tctcaagcaa atctaattgt aacagaactt ggagtaattg aggttattaa   1440
tgatggttta cttctcactg aaattaataa aaacacaacc attgatgaaa taaggtctt    1500
aactgctgca gatttactca tatccaatga acttagaccc atggctgttt agcatgc     1557

<210> SEQ ID NO 15
<211> LENGTH: 968
<212> TYPE: DNA
<213> ORGANISM: Clostridium acetobutylicum

<400> SEQUENCE: 15
gcatgccatc ggaagctgtg gtatggctgt gcaggtcgta aatcactgca taattcgtgt     60
cgctcaaggc gcactcccgt tctggataat gttttttgcg ccgacatcat aacggttctg    120
gcaaatattc tgaaatgagc tgttgacaat taatcatcgg ctcgtataat gtgtggaatt    180
gtgagcggat aacaatttca cacaggaaac aaaggaggag tgtgttgatg ttaaaggatg    240
aagtaattaa acaaattagc acgccattaa cttcgcctgc atttcctaga ggaccctata    300
aatttcataa tcgtgagtat tttaacattg tatatcgtac agatatggat gcacttcgta    360
aagttgtgcc agagccttta gaaattgatg agcccttagt caggtttgaa attatggcaa    420
tgcatgatac gagtggactt ggttgttata cagaaagcgg acaggctatt cccgtaagct    480
ttaatggagt taagggagat tatcttcata tgatgtattt agataatgag cctgcaattg    540
cagtaggaag ggaattaagt gcatatccta aaaagctcgg gtatccaaag ctttttgtgg    600
attcagatac tttagtagga actttagact atggaaaact tagagttgcg acagctacaa    660
tggggtacaa acataaagcc ttagatgcta atgaagcaaa ggatcaaatt tgtcgcccta    720
attatatgtt gaaataata cccaattatg atggaagccc tagaatatgt gagcttataa    780
atgcgaaaat cacagatgtt accgtacatg aagcttggac aggaccaact cgactgcagt    840
tatttgatca cgctatggcg ccacttaatg atttgccagt aaaagagatt gtttctagct    900
ctcacattct tgcagatata atattgccta gagctgaagt tatatatgat tatcttaagt    960
aacccggg                                                             968

<210> SEQ ID NO 16
<211> LENGTH: 1290
<212> TYPE: DNA
<213> ORGANISM: Clostridium beijerinckii

<400> SEQUENCE: 16
```

-continued

```
cccgggccat cggaagctgt ggtatggctg tgcaggtcgt aaatcactgc ataattcgtg      60
tcgctcaagg cgcactcccg ttctggataa tgttttttgc gccgacatca taacggttct     120
ggcaaatatt ctgaaatgag ctgttgacaa ttaatcatcg gctcgtataa tgtgtggaat     180
tgtgagcgga taacaatttc acacaggaaa caaggagga gtgtgttgat gaaaggtttt      240
gcaatgctag gtattaataa gttaggatgg atcgaaaaag aaaggccagt tgcgggttca     300
tatgatgcta ttgtacgccc attagcagta tctccgtgta catcagatat acatactgtt     360
tttgagggag ctcttggaga taggaagaat atgatttag gcatgaagc tgtaggtgaa       420
gttgttgaag taggaagtga agtgaaggat tttaaacctg gtgacagagt tatagttcct     480
tgtacaactc cagattggag atctttggaa gttcaagctg gttttcaaca gcactcaaac     540
ggtatgctcg caggatggaa attttcaaat ttcaaggatg gagttttgg tgaatatttt      600
catgtaaatg atgcggatat gaatcttgcg attctaccta agacatgcc attagaaaat     660
gctgttatga taacagatat gatgactact ggatttcatg gagcagaact tgcagatatt     720
caaatgggtt caagtgttgt ggtaattggc attggagctg ttggcttaat gggaatagca     780
ggtgctaaat tacgtggagc aggtagaata attggagtgg ggagcaggcc gatttgtgtt     840
gaggctgcaa aattttatgg agcaacagat attctaaatt ataaaaatgg tcatatagtt     900
gatcaagtta tgaaattaac gaatggaaaa ggcgttgacc gcgtaattat ggcaggcgt      960
ggttctgaaa cattatccca agcagtatct atggttaaac caggaggaat aatttctaat    1020
ataaattatc atggaagtgg agatgcttta ctaataccac gtgtagaatg gggatgtgga    1080
atggctcaca agactataaa aggaggtctt tgtcctgggg gacgtttgag agcagaaatg    1140
ttaagagata tggtagtata taatcgtgtt gatctaagta aattagttac acatgtatat    1200
catggatttg atcacataga agaagcactg ttattaatga agacaagcc aaaagactta    1260
attaaagcag tagttatatt ataaaagctt                                     1290
```

<210> SEQ ID NO 17
<211> LENGTH: 27
<212> TYPE: DNA
<213> ORGANISM: Artificial sequence
<220> FEATURE:
<223> OTHER INFORMATION: Primer

<400> SEQUENCE: 17

```
tcgagctcag gcagccatcg gaagctg                                         27
```

<210> SEQ ID NO 18
<211> LENGTH: 31
<212> TYPE: DNA
<213> ORGANISM: Artificial sequence
<220> FEATURE:
<223> OTHER INFORMATION: Primer

<400> SEQUENCE: 18

```
ttgcatgcca catagcagaa ctttaaaagt g                                    31
```

<210> SEQ ID NO 19
<211> LENGTH: 5018
<212> TYPE: DNA
<213> ORGANISM: Artificial sequence
<220> FEATURE:
<223> OTHER INFORMATION: Expression vector pCRC200

<400> SEQUENCE: 19

```
atgaccatga ttacgaatta attcgagctc aggcagccat cggaagctgt ggtatggctg     60
```

-continued

```
tgcaggtcgt aaatcactgc ataattcgtg tcgctcaagg cgcactcccg ttctggataa    120
tgttttttgc gccgacatca taacggttct ggcaaatatt ctgaaatgag ctgttgacaa    180
ttaatcatcg gctcgtataa tgtgtggaat tgtgagcgga taacaatttc acacaggaaa    240
cagaattccc ggggatccgt cgacctgcag ccaagcttgg ctgttttggc ggatgagaga    300
agattttcag cctgatacag attaaatcag aacgcagaag cggtctgata aaacagaatt    360
tgcctggcgg cagtagcgcg gtggtcccac ctgaccccat gccgaactca gaagtgaaac    420
gccgtagcgc cgatggtagt gtggggtctc cccatgcgag agtagggaac tgccaggcat    480
caaataaaac gaaaggctca gtcgaaagac tgggcctttc gttttatctg ttgtttgtcg    540
gtgaacgctc tcctgagtag gacaaatccg ccgggagcgg atttgaacgt tgcgaagcaa    600
cggcccggag ggtggcgggc aggacgcccg ccataaactg ccaggcatca aattaagcag    660
aaggccatcc tgacggatgg ccttttttgcg tttctacaaa ctcttttgtt tattttttcta   720 aatacattca aatatgtatc cgctcatgag acaataaccc tgataaatgc ttcaataata    780
ttgaaaaagg aagagtatga gtattcaaca tttccgtgtc gcccttattc cctttttttgc    840 ggcattttgc cttcctgttt ttgctcaccc agaaacgctg gtgaaagtaa agatgctga    900 agatcagttg ggtgcacgag tgggttacat cgaactggat ctcaacagcg gtaagatcct    960 tgagagttt cgccccgaag aacgttttcc aatgatgagc acttttaaag ttctgctatg   1020
tggcatgcaa gctagcttgg cactggccgt cgttttacaa cgtcgtgact gggaaaaccc   1080
tggcgttacc caacttaatc gccttgcagc acatccccct ttcgccagct ggcgtaatag   1140
cgaagaggcc cgcaccgatc gcccttccca acagttgcgc agcctgaatg gcgaatgagc   1200
ttcttccgct tcctcgctca ctgactcgct gcgctcggtc gttcggctgc ggcgagcggt   1260
atcagctcac tcaaaggcgg taatacggtt atccacagaa tcaggggata acgcaggaaa   1320
gaacatgtga gcaaaaggcc agcaaaaggc caggaaccgt aaaaaggccg cgttgctggc   1380 gttttttccat aggctccgcc cccctgacga gcatcacaaa aatcgacgct caagtcagag   1440
gtggcgaaac ccgacaggac tataaagata ccaggcgttt ccccctggaa gctccctcgt   1500
gcgctctcct gttccgaccc tgccgcttac cggatacctg tccgcctttc tcccttcggg   1560
aagcgtggcg ctttctcaat gctcacgctg taggtatctc agttcggtgt aggtcgttcg   1620
ctccaagctg ggctgtgtgc acgaaccccc cgttcagccc gaccgctgcg ccttatccgg   1680
taactatcgt cttgagtcca acccggtaag acacgactta tcgccactgg cagcagccac   1740
tggtaacagg attagcagag cgaggtatgt aggcggtgct acagagttct tgaagtggtg   1800
gcctaactac ggctacacta aaggacagt atttggtatc tgcgctctgc tgaagccagt   1860
taccttcgga aaaagagttg gtagctcttg atccggcaaa caaaccaccg ctggtagcgg   1920
tggttttttt gtttgcaagc agcagattac gcgcagaaaa aaaggatctc aagaagatcc   1980
tttgatcttt tctacggggt ctgacgctca gtggaacgat aacacatgca gtcatgtcgt   2040
gctaatgtgt aaaacatgta catgcagatt gctgggggtg caggggggcgg agccacccctg  2100 tccatgcggg gtgtggggct tgccccgccg gtacagacag tgagcaccgg ggcacctagt   2160
cgcggatacc cccctaggt atcggacacg taaccctccc atgtcgatgc aaatctttaa   2220
cattgagtac gggtaagctg gcacgcatag ccaagctagg cggccaccaa acaccactaa   2280
aaattaatag tccctagaca agacaaaccc ccgtgcgagc taccaactca tatgcacggg   2340
ggccacataa cccgaagggg tttcaattga caaccatagc actagctaag acaacgggca   2400
caacacccgc acaaactcgc actgcgcaac cccgcacaac atcgggtcta ggtaacactg   2460
```

```
aaatagaagt gaacacctct aaggaaccgc aggtcaatga gggttctaag gtcactcgcg    2520
ctagggcgtg gcgtaggcaa aacgtcatgt acaagatcac caatagtaag gctctggcgg    2580
ggtgccatag gtggcgcagg gacgaagctg ttgcggtgtc ctggtcgtct aacggtgctt    2640
cgcagtttga gggtctgcaa aactctcact ctcgctgggg gtcacctctg gctgaattgg    2700
aagtcatggg cgaacgccgc attgagctgg ctattgctac taagaatcac ttggcggcgg    2760
gtggcgcgct catgatgttt gtgggcactg ttcgacacaa ccgctcacag tcatttgcgc    2820
aggttgaagc gggtattaag actgcgtact cttcgatggt gaaaacatct cagtggaaga    2880
aagaacgtgc acggtacggg gtggagcaca cctatagtga ctatgaggtc acagactctt    2940
gggcgaacgg ttggcacttg caccgcaaca tgctgttgtt cttggatcgt ccactgtctg    3000
acgatgaact caaggcgttt gaggattcca tgttttcccg ctggtctgct ggtgtggtta    3060
aggccggtat ggacgcgcca ctgcgtgagc acggggtcaa acttgatcag gtgtctacct    3120
ggggtggaga cgctgcgaaa atggcaacct acctcgctaa gggcatgtct caggaactga    3180
ctggctccgc tactaaaacc gcgtctaagg ggtcgtacac gccgtttcag atgttggata    3240
tgttggccga tcaaagcgac gccggcgagg atatggacgc tgttttggtg gctcggtggc    3300
gtgagtatga ggttggttct aaaaacctgc gttcgtcctg gtcacgtggg gctaagcgtg    3360
ctttgggcat tgattacata gacgctgatg tacgtcgtga aatggaagaa gaactgtaca    3420
agctcgccgg tctggaagca ccggaacggg tcgaatcaac ccgcgttgct gttgctttgg    3480
tgaagcccga tgattggaaa ctgattcagt ctgatttcgc ggttaggcag tacgttctag    3540
attgcgtgga taaggctaag gacgtggccg ctgcgcaacg tgtcgctaat gaggtgctgg    3600
caagtctggg tgtggattcc accccgtgca tgatcgttat ggatgatgtg gacttggacg    3660
cggttctgcc tactcatggg gacgctacta agcgtgatct gaatgcggcg gtgttcgcgg    3720
gtaatgagca gactattctt cgcacccact aaaagcggca taaaccccgt tcgatatttt    3780
gtgcgatgaa tttatggtca atgtcgcggg ggcaaactat gatgggtctt gttgtgttat    3840
ctccgtcgaa cggaagatca cttcgcagaa taaataaatc ctggtgtccc tgttgatacc    3900
gggaagccct gggccaactt ttggcgaaaa tgagacgttg atcggcacgt aagaggttcc    3960
aactttcacc ataatgaaat aagatcacta ccgggcgtat ttttgagtt atcgagattt     4020 tcaggagcta aggaagctaa aatggagaaa aaatcactg gatataccac cgttgatata    4080
tcccaatggc atcgtaaaga acattttgag gcatttcagt cagttgctca atgtacctat    4140
aaccagaccg ttcagctgga tattacggcc ttttttaaaga ccgtaaagaa aaataagcac    4200
aagttttatc cggcctttat tcacattctt gcccgcctga tgaatgctca tccggaattt    4260
cgtatggcaa tgaaagacgg tgagctgtg atatgggata tgttcaccc ttgttacacc     4320 gttttccatg agcaaactga aacgttttca tcgctctgga gtgaatacca cgacgatttc    4380
cggcagtttc tacacatata ttcgcaagat gtggcgtgtt acggtgaaaa cctggcctat    4440
ttccctaaag ggtttattga gaatatgttt ttcgtctcag ccaatccctg ggtgagtttc    4500
accagttttg atttaaacgt ggccaatatg acaacttct tcgcccccgt tttcaccatg     4560
ggcaaatatt atacgcaagg cgacaaggtg ctgatgccgc tggcgattca ggttcatcat    4620
gccgtctgtg atggcttcca tgtcggcaga atgcttaatg aattacaaca gtactgcgat    4680
gagtggcagg gcggggcgta attttttta ggcagttatt ggtgccctta aacgcctggt     4740
gctacgcctg aataagtgat aataagcgga tgaatggcag aaattcagct tggcccagtg    4800
ccaagctcca atacgcaaac cgcctctccc cgcgcgttgg ccgattcatt aatgcagctg    4860
```

| | |
|---|---:|
| gcacgacagg tttcccgact ggaaagcggg cagtgagcgc aacgcaatta atgtgagtta | 4920 |
| gctcactcat taggcacccc aggctttaca ctttatgctt ccggctcgta tgttgtgtgg | 4980 |
| aattgtgagc ggataacaat ttcacacagg aaacagct | 5018 |

<210> SEQ ID NO 20
<211> LENGTH: 9552
<212> TYPE: DNA
<213> ORGANISM: Artificial sequence
<220> FEATURE:
<223> OTHER INFORMATION: Expression plasmid pCRC201

<400> SEQUENCE: 20

| | |
|---|---:|
| ggtcctcgcc gaaaatgacc cagagcgctg ccggcacctg tcctacgagt tgcatgataa | 60 |
| agaagacagt cataagtgcg gcgacgatag tcatgccccg cgcccaccgg aaggagctga | 120 |
| ctgggttgaa ggctctcaag ggcatcggtc gacgctctcc cttatgcgac tcctgcatta | 180 |
| ggaagcagcc cagtagtagg ttgaggccgt tgagcaccgc cgccgcaagg aatggtgcat | 240 |
| gcaaggagat ggcgcccaac agtccccccgg ccacggggcc tgccaccata cccacgccga | 300 |
| aacaagcgct catgagcccg aagtggcgag cccgatcttc cccatcggtg atgtcggcga | 360 |
| tataggcgcc agcaaccgca cctgtggcgc cggtgatgcc ggccacgatg cgtccggcgt | 420 |
| agaggatccg ggcttatcga ctgcacggtg caccaatgct tctggcgtca ggcagccatc | 480 |
| ggaagctgtg gtatggctgt gcaggtcgta aatcactgca taattcgtgt cgctcaaggc | 540 |
| gcactcccgt tctggataat gttttttgcg ccgacatcat aacggttctg gcaaatattc | 600 |
| tgaaatgagc tgttgacaat taatcatcgg ctcgtataat gtgtggaatt gtgagcggat | 660 |
| aacaatttca cacaggaaac agaattcaaa ggaggagtgt gttgatgaaa gaagttgtaa | 720 |
| tagctagtgc agtaagaaca gcgattggat cttatggaaa gtctcttaag gatgtaccag | 780 |
| cagtagattt aggagctaca gctataaagg aagcagttaa aaaagcagga ataaaaccag | 840 |
| aggatgttaa tgaagtcatt ttaggaaatg ttcttcaagc aggtttagga cagaatccag | 900 |
| caagacaggc atcttttaaa gcaggattac cagttgaaat tccagctatg actattaata | 960 |
| aggtttgtgg ttcaggactt agaacagtta gcttagcagc acaaattata aaagcaggag | 1020 |
| atgctgacgt aataatagca ggtggtatgg aaaatatgtc tagagctcct tacttagcga | 1080 |
| ataacgctag atgggggatat agaatgggaa acgctaaatt tgttgatgaa atgatcactg | 1140 |
| acggattgtg ggatgcattt aatgattacc acatgggaat aacagcagaa aacatagctg | 1200 |
| agagatggaa catttcaaga gaagaacaag atgagtttgc tcttgcatca aaaaaaaag | 1260 |
| ctgaagaagc tataaaatca ggtcaattta aagatgaaat agttcctgta gtaattaaag | 1320 |
| gcagaaaggg agaaactgta gttgatacag atgagcaccc tagatttgga tcaactatag | 1380 |
| aaggacttgc aaaattaaaa cctgccttca aaaagatgg aacagttaca gctggtaatg | 1440 |
| catcaggatt aaatgactgt gcagcagtac ttgtaatcat gagtgcagaa aaagctaaag | 1500 |
| agcttggagt aaaaccactt gctaagatag tttcttatgg ttcagcagga gttgacccag | 1560 |
| caataatggg atatgaccct ttctatgcaa caaaagcagc tattgaaaaa gcaggttgga | 1620 |
| cagttgatga attagattta atagaatcaa atgaagcttt tgcagctcaa agtttagcag | 1680 |
| tagcaaaaga tttaaaattt gatatgaata agtaaatgt aaatggagga gctattgccc | 1740 |
| ttggtcatcc aattggagca tcaggtgcaa gaatactcgt tactcttgta cacgcaatgc | 1800 |
| aaaaaagaga tgcaaaaaaa ggcttagcaa ctttatgtat aggtggcgga caaggaacag | 1860 |
| caatattgct agaaaagtgc tagggatccc catcggaagc tgtggtatgg ctgtgcaggt | 1920 |

```
cgtaaatcac tgcataattc gtgtcgctca aggcgcactc ccgttctgga taatgttttt       1980
tgcgccgaca tcataacggt tctggcaaat attctgaaat gagctgttga caattaatca       2040
tcggctcgta taatgtgtgg aattgtgagc ggataacaat ttcacacagg aaacaaagga       2100
ggagtgtgtt gatgaactct aaaataatta gatttgaaaa tttaaggtca ttctttaaag       2160
atgggatgac aattatgatt ggaggttttt taaactgtgg cactccaacc aaattaattg       2220 atttttagt taatttaaat ataaagaatt taacgattat aagtaatgat acatgttatc       2280
ctaatacagg tattggtaag ttaatatcaa ataatcaagt aaaaaagctt attgcttcat       2340
atataggcag caacccagat actggcaaaa aacttttaa taatgaactt gaagtagagc       2400
tctctcccca aggaactcta gtggaaagaa tacgtgcagg cggatctggc ttaggtggtg       2460
tactaactaa aacaggttta ggaactttga ttgaaaaagg aaagaaaaaa atatctataa       2520
atggaacgga atatttgtta gagctacctc ttacagccga tgtagcatta attaaaggta       2580
gtattgtaga tgaggccgga aacaccttct ataaaggtac tactaaaaac tttaatccct       2640
atatggcaat ggcagctaaa accgtaatag ttgaagctga aaatttagtt agctgtgaaa       2700
aactagaaaa ggaaaaagca atgaccccg gagttcttat aaattatata gtaaaggagc       2760
ctgcataaaa tgattaatga taaaaaccta gcgaaagaaa taatagccaa aagagttgca       2820
agagaattaa aaaatggtca acttgtaaac ttaggtgtag gtcttcctac catgttgca       2880 gattatatac caaaaatttt caaaattact ttccaatcag aaaacggaat agttggaatg       2940
ggcgctagtc ctaaaataaa tgaggcagat aaagatgtag taaatgcagg aggagactat       3000
acaacagtac ttcctgacgg cacatttttc gatagctcag tttcgttttc actaatccgt       3060
ggtggtcacg tagatgttac tgttttaggg gctctccagg tagatgaaaa gggtaatata       3120
gccaattgga ttgttcctgg aaaaatgctc tctggtatgg gtggagctat ggatttagta       3180
aatggagcta agaaagtaat aattgcaatg agacatacaa ataaaggtca acctaaaatt       3240
ttaaaaaaat gtacacttcc cctcacggca aagtctcaag caaatctaat tgtaacagaa       3300
cttggagtaa ttgaggttat taatgatggt ttacttctca ctgaaattaa taaaaacaca       3360
accattgatg aaataaggtc tttaactgct gcagatttac tcatatccaa tgaacttaga       3420
cccatggctg tttagcatgc catcggaagc tgtggtatgg ctgtgcaggt cgtaaatcac       3480
tgcataattc gtgtcgctca aggcgcactc ccgttctgga taatgttttt tgcgccgaca       3540
tcataacggt tctggcaaat attctgaaat gagctgttga caattaatca tcggctcgta       3600
taatgtgtgg aattgtgagc ggataacaat ttcacacagg aaacaaagga ggagtgtgtt       3660
gatgttaaag gatgaagtaa ttaaacaaat tagcacgcca ttaacttcgc ctgcatttcc       3720
tagaggaccc tataaatttc ataatcgtga gtattttaac attgtatatc gtacagatat       3780
ggatgcactt cgtaaagttg tgccagagcc tttagaaatt gatgagcctt agtcaggtt       3840 tgaaattatg gcaatgcatg atacgagtgg acttggttgt tatacagaaa gcggacaggc       3900
tattcccgta agctttaatg gagttaaggg agattatctt catatgatgt atttagataa       3960
tgagcctgca attgcagtag aagggaatt aagtgcatat cctaaaaagc tcgggtatcc       4020
aaagcttttt gtggattcag atactttagt aggaacttta gactatggaa aacttagagt       4080
tgcgacagct acaatgggt acaaacataa agccttagat gctaatgaag caaaggatca       4140
aatttgtcgc cctaattata tgttgaaaat aatacccaat tatgatggaa gccctagaat       4200
atgtgagctt ataaatgcga aaatcacaga tgttaccgta catgaagctt ggacaggacc       4260
aactcgactg cagttatttg atcacgctat ggcgccactt aatgatttgc cagtaaaaga       4320
```

```
gattgtttct agctctcaca ttcttgcaga tataatattg cctagagctg aagttatata   4380
tgattatctt aagtaacccg ggccatcgga agctgtggta tggctgtgca ggtcgtaaat   4440
cactgcataa ttcgtgtcgc tcaaggcgca ctcccgttct ggataatgtt ttttgcgccg   4500
acatcataac ggttctggca atattctga aatgagctgt tgacaattaa tcatcggctc    4560
gtataatgtg tggaattgtg agcggataac aatttcacac aggaaacaaa ggaggagtgt   4620
gttgatgaaa ggttttgcaa tgctaggtat taataagtta ggatggatcg aaaaagaaag   4680
gccagttgcg ggttcatatg atgctattgt acgcccatta gcagtatctc cgtgtacatc   4740
agatatacat actgtttttg agggagctct tggagatagg aagaatatga ttttagggca   4800
tgaagctgta ggtgaagttg ttgaagtagg aagtgaagtg aaggatttta aacctggtga   4860
cagagttata gttccttgta caactccaga ttggagatct ttggaagttc aagctggttt   4920
tcaacagcac tcaaacggta tgctcgcagg atggaaattt tcaaatttca aggatggagt   4980
ttttggtgaa tattttcatg taaatgatgc ggatatgaat cttgcgattc tacctaaaga   5040
catgccatta gaaaatgctg ttatgataac agatatgatg actactggat tcatggagc    5100
agaacttgca gatattcaaa tgggttcaag tgttgtggta attggcattg gagctgttgg   5160
cttaatggga atagcaggtg ctaaattacg tggagcaggt agaataattg gagtggggag   5220
caggccgatt tgtgttgagg ctgcaaaatt ttatggagca acagatattc taaattataa   5280
aaatggtcat atagttgatc aagttatgaa attaacgaat ggaaaaggcg ttgaccgcgt   5340
aattatggca ggcggtggtt ctgaaacatt atcccaagca gtatctatgg ttaaaccagg   5400
aggaataatt tctaatataa attatcatgg aagtggagat gctttactaa taccacgtgt   5460
agaatgggga tgtggaatgg ctcacaagac tataaaagga ggtctttgtc ctgggggacg   5520
tttgagagca gaaatgttaa gagatatggt agtatataat cgtgttgatc taagtaaatt   5580
agttacacat gtatatcatg gatttgatca catagaagaa gcactgttat taatgaaaga   5640
caagccaaaa gacttaatta aagcagtagt tatattataa agcttggctg ttttggcgga   5700
tgagagaaga ttttcagcct gatacagatt aaatcagaac gcagaagcgg tctgataaaa   5760
cagaatttgc ctggcggcag tagcgcggtg gtcccacctg accccatgcc gaactcagaa   5820
gtgaaacgcc gtagcgccga tggtagtgtg gggtctcccc atgcgagagt agggaactgc   5880
caggcatcaa ataaaacgaa aggctcagtc gaaagactgg gcctttcgtt ttatctgttg   5940
tttgtcggtg aacgctctcc tgagtaggac aaatccgccg ggagcggatt tgaacgttgc   6000
gaagcaacgg cccggagggt ggcgggcagg acgcccgcca taaactgcca ggcatcaaat   6060
taagcagaag gccatcctga cggatggcct ttttgcgttt ctacaaactc ttttgtttat   6120
ttttctaaat acattcaaat atgtatccgc tcatgagaca ataaccctga taatgcttc    6180
aataatattg aaaaggaag agtatgagta ttcaacattt ccgtgtcgcc cttattccct   6240
ttttttgcggc attttgcctt cctgtttttg ctcacccaga aacgctggtg aaagtaaaag   6300
atgctgaaga tcagttgggt gcacgagtgg gttacatcga actggatctc aacagcggta   6360
agatccttga gagttttcgc cccgaagaac gttttccaat gatgagcact tttaaagttc   6420
tgctatgtgg cgcggtatta tcccgtgttg acgccgggca agagcaactc ggtcgccgca   6480
tacactattc tcagaatgac ttggttgagt actcaccagt cacagaaaag catcttacgg   6540
atggcatgac agtaagagaa ttatgcagtg ctgccataac catgagtgat aacactgcgg   6600
ccaacttact tctgacaacg atcggaggac cgaaggagct aaccgctttt ttgcacaaca   6660
tgggggatca tgtaactcgc cttgatcgtt gggaaccgga gctgaatgaa gccataccaa   6720
```

-continued

| | |
|---|---|
| acgacgagcg tgacaccacg atgctgtagc aatggcaaca acgttgcgca aactattaac | 6780 |
| tggcgaacta cttactctag cttcccggca acaattaata gactggatgg aggcggataa | 6840 |
| agttgcagga ccacttctgc gctcggccct tccggctggc tggtttattg ctgataaatc | 6900 |
| tggagccggt gagcgtgggt ctcgcggtat cattgcagca ctggggccag atggtaagcc | 6960 |
| ctcccgtatc gtagttatct acacgacggg gagtcaggca actatggatg aacgaaatag | 7020 |
| acagatcgct gagataggtg cctcactgat taagcattgg taactgtcag accaagttta | 7080 |
| ctcatatata ctttagattg atttaaaact tcatttttaa tttaaaagga tctaggtgaa | 7140 |
| gatcctttt gataatctca tgaccaaaat cccttaacgt gagttttcgt tccactgagc | 7200 |
| gtcagacccc gtagaaaaga tcaaaggatc ttcttgagat cctttttttc tgcgcgtaat | 7260 |
| ctgctgcttg caaacaaaaa aaccaccgct accagcggtg gtttgtttgc cggatcaaga | 7320 |
| gctaccaact cttttccga aggtaactgg cttcagcaga gcgcagatac caaatactgt | 7380 |
| ccttctagtg tagccgtagt taggccacca cttcaagaac tctgtagcac cgcctacata | 7440 |
| cctcgctctg ctaatcctgt taccagtggc tgctgccagt ggcgataagt cgtgtcttac | 7500 |
| cgggttggac tcaagacgat agttaccgga taaggcgcag cggtcgggct gaacggggggg | 7560 |
| ttcgtgcaca gcccagct tggagcgaac gacctacacc gaactgagat acctacagcg | 7620 |
| tgagcattga gaaagcgcca cgcttcccga agggagaaag gcggacaggt atccggtaag | 7680 |
| cggcagggtc ggaacaggag agcgcacgag ggagcttcca gggggaaacg cctggtatct | 7740 |
| ttatagtcct gtcgggtttc gccacctctg acttgagcgt cgattttgt gatgctcgtc | 7800 |
| aggggggcgg agcctatgga aaaacgccag caacgcggcc ttttacggt tcctggcctt | 7860 |
| ttgctggcct tttgctcaca tgttctttcc tgcgttatcc cctgattctg tggataaccg | 7920 |
| tattaccgcc tttgagtgag ctgataccgc tcgccgcagc cgaacgaccg agcgcagcga | 7980 |
| gtcagtgagc gaggaagcgg aagagcgcct gatgcggtat tttctcctta cgcatctgtg | 8040 |
| cggtatttca caccgcatat ggtgcactct cagtacaatc tgctctgatg ccgcatagtt | 8100 |
| aagccagtat acactccgct atcgctacgt gactgggtca tggctgcgcc ccgacacccg | 8160 |
| ccaacacccg ctgacgcgcc ctgacgggct tgtctgctcc cggcatccgc ttacagacaa | 8220 |
| gctgtgaccg tctccgggag ctgcatgtgt cagaggtttt caccgtcatc accgaaacgc | 8280 |
| gcgaggcagc tgcggtaaag ctcatcagcg tggtcgtgaa gcgattcaca gatgtctgcc | 8340 |
| tgttcatccg cgtccagctc gttgagtttc tccagaagcg ttaatgtctg gcttctgata | 8400 |
| aagcgggcca tgttaagggc ggttttttcc tgtttggtca ctgatgcctc cgtgtaaggg | 8460 |
| ggatttctgt tcatgggggt aatgataccg atgaaacgag agaggatgct cacgatacgg | 8520 |
| gttactgatg atgaacatgc ccggttactg gaacgttgtg agggtaaaca actggcggta | 8580 |
| tggatgcggc gggaccagag aaaaatcact cagggtcaat gccagcgctt cgttaataca | 8640 |
| gatgtaggtg ttccacaggg tagccagcag catcctgcga tgcagatccg gaacataatg | 8700 |
| gtgcagggcg ctgacttccg cgtttccaga ctttacgaaa cacggaaacc gaagaccatt | 8760 |
| catgttgttg ctcaggtcgc agacgttttg cagcagcagt cgcttcacgt tcgctcgcgt | 8820 |
| atcggtgatt cattctgcta accagtaagg caaccccgcc agcctagccg gtcctcaac | 8880 |
| gacaggagca cgatcatgcg cacccgtggc caggacccaa cgctgcccga gatgcgccgc | 8940 |
| gtgcggctgc tggagatggc ggacgcgatg gatatgttct gccaagggtt ggtttgcgca | 9000 |
| ttcacagttc tccgcaagaa ttgattggct ccaattcttg gagtggtgaa tccgttagcg | 9060 |
| aggtgccgcc ggcttccatt caggtcgagg tggcccggct ccatgcaccg cgacgcaacg | 9120 |

-continued

```
cggggaggca gacaaggtat agggcggcgc ctacaatcca tgccaacccg ttccatgtgc    9180
tcgccgaggc ggcataaatc gccgtgacga tcagcggtcc agtgatcgaa gttaggctgg    9240
taagagccgc gagcgatcct tgaagctgtc cctgatggtc gtcatctacc tgcctggaca    9300
gcatggcctg caacgcgggc atcccgatgc cgccggaagc gagaagaatc ataatgggga    9360
aggccatcca gcctcgcgtc gcgaacgcca gcaagacgta gcccagcgcg tcggccgcca    9420
tgccggcgat aatggcctgc ttctcgccga aacgtttggt ggcgggacca gtgacgaagg    9480
cttgagcgag ggcgtgcaag attccgaata ccgcaagcga caggccgatc atcgtcgcgc    9540
tccagcgaaa gc                                                       9552
```

<210> SEQ ID NO 21
<211> LENGTH: 28
<212> TYPE: DNA
<213> ORGANISM: Artificial sequence
<220> FEATURE:
<223> OTHER INFORMATION: Primer

<400> SEQUENCE: 21

```
gtcgacttat aatataacta ctgcttta                                        28
```

<210> SEQ ID NO 22
<211> LENGTH: 10011
<212> TYPE: DNA
<213> ORGANISM: Artificial sequence
<220> FEATURE:
<223> OTHER INFORMATION: Expression plasmid pCRC202

<400> SEQUENCE: 22

```
atgaccatga ttacgaatta attcgagctc aggcagccat cggaagctgt ggtatggctg      60
tgcaggtcgt aaatcactgc ataattcgtg tcgctcaagg cgcactcccg ttctggataa    120
tgttttttgc gccgacatca taacggttct ggcaaatatt ctgaaatgag ctgttgacaa    180
ttaatcatcg gctcgtataa tgtgtggaat tgtgagcgga taacaatttc acacaggaaa    240
cagaattccc gggaattcaa ggaggagtg tgttgatgaa agaagttgta atagctagtg     300
cagtaagaac agcgattgga tcttatggaa agtctcttaa ggatgtacca gcagtagatt    360
taggagctac agctataaag gaagcagtta aaaagcagg aataaaacca gaggatgtta     420
atgaagtcat tttaggaaat gttcttcaag caggtttagg acagaatcca gcaagacagg    480
catcttttaa agcaggatta ccagttgaaa ttccagctat gactattaat aaggtttgtg    540
gttcaggact tagaacagtt agcttagcag cacaaatatt aaaagcagga gatgctgacg    600
taataatagc aggtggtatg gaaaatatgt ctagagctcc ttacttagcg aataacgcta    660 gatgggata tagaatggga aacgctaaat tgttgatga atgatcact gacggattgt       720 gggatgcatt taatgattac cacatgggaa taacagcaga aacatagct gagagatgga     780 acatttcaag agaagaacaa gatgagtttg ctccttgcatc acaaaaaaaa gctgaagaag    840
ctataaaatc aggtcaattt aaagatgaaa tagttcctgt agtaattaaa ggcagaaagg    900
gagaaactgt agttgataca gatgagcacc ctagatttgg atcaactata gaaggacttg    960
caaaattaaa acctgccttc aaaaagatg gaacagttac agctggtaat gcatcaggat    1020
taaatgactg tgcagcagta cttgtaatca tgagtgcaga aaaagctaaa gagcttggag    1080
taaaaccact tgctaagata gtttcttatg gttcagcagg agttgaccca gcaataatgg    1140 gatatgacc tttctatgca acaaaagcag ctattgaaaa agcaggttgg acagttgatg    1200
aattagattt aatagaatca aatgaagctt ttgcagctca aagtttagca gtagcaaaag    1260
```

```
atttaaaatt tgatatgaat aaagtaaatg taaatggagg agctattgcc cttggtcatc    1320
caattggagc atcaggtgca agaatactcg ttactcttgt acacgcaatg caaaaaagag    1380
atgcaaaaaa aggcttagca actttatgta taggtggcgg acaaggaaca gcaatattgc    1440
tagaaaagtg ctagggatcc ccatcggaag ctgtggtatg gctgtgcagg tcgtaaatca    1500
ctgcataatt cgtgtcgctc aaggcgcact cccgttctgg ataatgtttt ttgcgccgac    1560
atcataacgg ttctggcaaa tattctgaaa tgagctgttg acaattaatc atcggctcgt    1620
ataatgtgtg gaattgtgag cggataacaa tttcacacag gaaacaaagg aggagtgtgt    1680
tgatgaactc taaaataatt agatttgaaa atttaaggtc attctttaaa gatgggatga    1740
caattatgat tggaggtttt ttaaactgtg gcactccaac caaattaatt gattttttag    1800
ttaatttaaa tataaagaat ttaacgatta taagtaatga tacatgttat cctaatacag    1860
gtattggtaa gttaatatca aataatcaag taaaaaagct tattgcttca tatataggca    1920
gcaacccaga tactggcaaa aaacttttta ataatgaact tgaagtagag ctctctcccc    1980
aaggaactct agtggaaaga atacgtgcag gcggatctgg cttaggtggt gtactaacta    2040
aaacaggttt aggaactttg attgaaaaag gaaagaaaaa aatatctata aatggaacgg    2100
aatatttgtt agagctacct cttacagccg atgtagcatt aattaaaggt agtattgtag    2160
atgaggccgg aaacaccttc tataaaggta ctactaaaaa ctttaatccc tatatggcaa    2220
tggcagctaa aaccgtaata gttgaagctg aaaatttagt tagctgtgaa aaactagaaa    2280
aggaaaaagc aatgacccccc ggagttctta taaattatat agtaaaggag cctgcataaa    2340
atgattaatg ataaaaacct agcgaaagaa ataatagcca aaagagttgc aagagaatta    2400
aaaaatggtc aacttgtaaa cttaggtgta ggtcttccta ccatggttgc agattatata    2460
ccaaaaaatt tcaaaattac tttccaatca gaaaacggaa tagttggaat gggcgctagt    2520
cctaaaataa atgaggcaga taaagatgta gtaaatgcag gaggagacta tacaacagta    2580
cttcctgacg gcacattttt cgatagctca gtttcgtttt cactaatccg tggtggtcac    2640
gtagatgtta ctgttttagg ggctctccag gtagatgaaa agggtaatat agccaattgg    2700
attgttcctg gaaaaatgct ctctggtatg ggtggagcta tggatttagt aaatggagct    2760
aagaaagtaa taattgcaat gagacataca aataaaggtc aacctaaaat tttaaaaaaa    2820
tgtacacttc ccctcacggc aaagtctcaa gcaaatctaa ttgtaacaga acttggagta    2880
attgaggtta ttaatgatgg tttacttctc actgaaatta ataaaaacac aaccattgat    2940
gaaataaggt ctttaactgc tgcagattta ctcatatcca atgaacttag acccatggct    3000
gtttagcatg ccatcggaag ctgtggtatg gctgtgcagg tcgtaaatca ctgcataatt    3060
cgtgtcgctc aaggcgcact cccgttctgg ataatgtttt ttgcgccgac atcataacgg    3120
ttctggcaaa tattctgaaa tgagctgttg acaattaatc atcggctcgt ataatgtgtg    3180
gaattgtgag cggataacaa tttcacacag gaaacaaagg aggagtgtgt tgatgttaaa    3240
ggatgaagta attaaacaaa ttagcacgcc attaacttcg cctgcatttc ctagaggacc    3300
ctataaattt cataatcgtg agtattttaa cattgtatat cgtacagata tggatgcact    3360
tcgtaaagtt gtgccagagc ctttagaaat tgatgagccc ttagtcaggt ttgaaattat    3420
ggcaatgcat gatacgagtg gacttggttg ttatacagaa gcggacagg ctattcccgt    3480 aagctttaat ggagttaagg gagattatct tcatatgatg tatttagata atgagcctgc    3540
aattgcagta ggaagggaat taagtgcata tcctaaaaag ctcgggtatc caaagctttt    3600
tgtggattca gatactttag taggaacttt agactatgga aaacttagag ttgcgacagc    3660
```

```
tacaatgggg tacaaacata aagccttaga tgctaatgaa gcaaaggatc aaatttgtcg    3720
ccctaattat atgttgaaaa taatacccaa ttatgatgaa agccctagaa tatgtgagct    3780
tataaatgcg aaaatcacag atgttaccgt acatgaagct tggacaggac caactcgact    3840
gcagttattt gatcacgcta tggcgccact taatgatttg ccagtaaaag agattgtttc    3900
tagctctcac attcttgcag atataatatt gcctagagct gaagttatat atgattatct    3960
taagtaaccc gggccatcgg aagctgtggt atggctgtgc aggtcgtaaa tcactgcata    4020
attcgtgtcg ctcaaggcgc actcccgttc tggataatgt ttttgcgcc gacatcataa     4080 cggttctggc aaatattctg aaatgagctg ttgacaatta atcatcggct cgtataatgt    4140
gtggaattgt gagcggataa caatttcaca caggaaacaa aggaggagtg tgttgatgaa    4200
aggttttgca atgctaggta ttaataagtt aggatggatc gaaaagaaa ggccagttgc     4260 gggttcatat gatgctattg tacgcccatt agcagtatct ccgtgtacat cagatataca    4320
tactgttttt gagggagctc ttggagatag aagaatatg atttagggc atgaagctgt      4380 aggtgaagtt gttgaagtag aagtgaagt gaaggatttt aaacctggtg acagagttat     4440
agttccttgt acaactccag attggagatc tttggaagtt caagctggtt ttcaacagca    4500
ctcaaacggt atgctcgcag gatggaaatt ttcaaatttc aaggatggag tttttggtga    4560
atattttcat gtaaatgatg cggatatgaa tcttgcgatt ctacctaaag acatgccatt    4620
agaaaatgct gttatgataa cagatatgat gactactgga tttcatggag cagaacttgc    4680
agatattcaa atgggttcaa gtgttgtggt aattggcatt ggagctgttg cttaatggg     4740 aatagcaggt gctaaattac gtggagcagg tagaataatt ggagtgggga gcaggccgat    4800
ttgtgttgag gctgcaaaat tttatggagc aacagatatt ctaaattata aaaatggtca    4860
tatagttgat caagttatga aattaacgaa tggaaaaggc gttgaccgcg taattatggc    4920
aggcggtggt tctgaaacat tatcccaagc agtatctatg gttaaaccag gaggaataat    4980
ttctaatata aattatcatg gaagtggaga tgctttacta ataccacgtg tagaatgggg    5040
atgtggaatg gctcacaaga ctataaaagg aggtctttgt cctgggggac gtttgagagc    5100
agaaatgtta agagatatgg tagtatataa tcgtgttgat ctaagtaaat tagttacaca    5160
tgtatatcat ggatttgatc acatagaaga agcactgtta ttaatgaaag acaagccaaa    5220
agacttaatt aaagcagtag ttatattata agtcgacctg cagccaagct tggctgtttt    5280
ggcggatgag agaagatttt cagcctgata cagattaaat cagaacgcag aagcggtctg    5340
ataaaacaga atttgcctgg cggcagtagc gcggtggtcc cacctgaccc catgccgaac    5400
tcagaagtga aacgccgtag cgccgatggt agtgtggggt ctccccatgc gagagtaggg    5460
aactgccagg catcaaataa aacgaaaggc tcagtcgaaa gactgggcct ttcgttttat    5520
ctgttgtttg tcggtgaacg ctctcctgag taggacaaat ccgccgggag cggatttgaa    5580
cgttgcgaag caacggcccg gagggtggcg ggcaggacgc ccgccataaa ctgccaggca    5640
tcaaattaag cagaaggcca tcctgacgga tggcctttt gcgtttctac aaactctttt      5700
gtttattttt ctaaatacat tcaaatatgt atccgctcat gagacaataa ccctgataaa    5760
tgcttcaata atattgaaaa aggaagagta tgagtattca acatttccgt gtcgccctta    5820
ttcccttttt tgcggcattt tgccttcctg tttttgctca cccagaaacg ctggtgaaag    5880
taaaagatgc tgaagatcag ttgggtgcac gagtgggtta catcgaactg gatctcaaca    5940
gcggtaagat ccttgagagt tttcgccccg aagaacgttt tccaatgatg agcactttta    6000
aagttctgct atgtggcatg caagctagct tggcactggc cgtcgtttta caacgtcgtg    6060
```

```
actgggaaaa ccctggcgtt acccaactta atcgccttgc agcacatccc cctttcgcca    6120
gctggcgtaa tagcgaagag gcccgcaccg atcgcccttc ccaacagttg cgcagcctga    6180
atggcgaatg agcttcttcc gcttcctcgc tcactgactc gctgcgctcg gtcgttcggc    6240
tgcggcgagc ggtatcagct cactcaaagg cggtaatacg gttatccaca gaatcagggg    6300
ataacgcagg aaagaacatg tgagcaaaag gccagcaaaa ggccaggaac cgtaaaaagg    6360
ccgcgttgct ggcgtttttc cataggctcc gcccccctga cgagcatcac aaaaatcgac    6420
gctcaagtca gaggtggcga aacccgacag gactataaag ataccaggcg tttccccctg    6480
gaagctccct cgtgcgctct cctgttccga cctgccgct taccggatac ctgtccgcct    6540
ttctcccttc gggaagcgtg gcgctttctc aatgctcacg ctgtaggtat ctcagttcgg    6600
tgtaggtcgt tcgctccaag ctgggctgtg tgcacgaacc cccgttcag cccgaccgct    6660 gcgccttatc cggtaactat cgtcttgagt ccaacccggt aagacacgac ttatcgccac    6720
tggcagcagc cactggtaac aggattagca gagcgaggta tgtaggcggt gctacagagt    6780
tcttgaagtg gtggcctaac tacggctaca ctagaaggac agtatttggt atctgcgctc    6840
tgctgaagcc agttaccttc ggaaaaagag ttggtagctc ttgatccggc aaacaaacca    6900
ccgctggtag cggtggtttt tttgtttgca agcagcagat tacgcgcaga aaaaaggat    6960 ctcaagaaga tcctttgatc ttttctacgg ggtctgacgc tcagtggaac gataacacat    7020
gcagtcatgt cgtgctaatg tgtaaaacat gtacatgcag attgctgggg gtgcagggg    7080 cggagccacc ctgtccatgc ggggtgtggg gcttgcccg ccggtacaga cagtgagcac    7140
cggggcacct agtcgcggat accccccta ggtatcggac acgtaaccct cccatgtcga    7200
tgcaaatctt taacattgag tacgggtaag ctggcacgca tagccaagct aggcggccac    7260
caaacaccac taaaaattaa tagtccctag acaagacaaa ccccgtgcg agctaccaac    7320 tcatatgcac gggggccaca taacccgaag gggtttcaat tgacaaccat agcactagct    7380
aagacaacgg gcacaacacc cgcacaaact cgcactgcgc aaccccgcac aacatcgggt    7440
ctaggtaaca ctgaaataga agtgaacacc tctaaggaac cgcaggtcaa tgagggttct    7500
aaggtcactc gcgctagggc gtggcgtagg caaaacgtca tgtacaagat caccaatagt    7560
aaggctctgg cggggtgcca taggtggcgc agggacgaag ctgttgcggt gtcctggtcg    7620
tctaacggtg cttcgcagtt tgagggtctg caaaactctc actctcgctg ggggtcacct    7680
ctggctgaat tggaagtcat gggcgaacgc cgcattgagc tggctattgc tactaagaat    7740
cacttggcgg cgggtggcgc gctcatgatg tttgtgggca ctgttcgaca caaccgctca    7800
cagtcatttg cgcaggttga agcgggtatt aagactgcgt actcttcgat ggtgaaaaca    7860
tctcagtgga agaagaaacg tgcacggtac ggggtgagc acacctatag tgactatgag    7920
gtcacagact cttgggcgaa cggttggcac ttgcaccgca acatgctgtt gttcttggat    7980
cgtccactgt ctgacgatga actcaaggcg tttgaggatt ccatgttttc ccgctggtct    8040
gctggtgtgg ttaaggccgg tatggacgcg ccactgcgtg agcacgggt caaacttgat    8100 caggtgtcta cctggggtgg agacgctgcg aaaatggcaa cctacctcgc taagggcatg    8160
tctcaggaac tgactggctc cgctactaaa accgcgtcta aggggtcgta cacgccgttt    8220
cagatgttgg atatgttggc cgatcaaagc gacgccggcg aggatatgga cgctgttttg    8280
gtggctcggt ggcgtgagta tgaggttggt tctaaaaacc tgcgttcgtc ctggtcacgt    8340
ggggctaagc gtgctttggg cattgattac atagacgctg atgtacgtcg tgaaatggaa    8400
gaagaactgt acaagctcgc cggtctggaa gcaccggaac gggtcgaatc aacccgcgtt    8460
```

```
gctgttgctt tggtgaagcc cgatgattgg aaactgattc agtctgattt cgcggttagg    8520
cagtacgttc tagattgcgt ggataaggct aaggacgtgg ccgctgcgca acgtgtcgct    8580
aatgaggtgc tggcaagtct gggtgtggat tccaccccgt gcatgatcgt tatggatgat    8640
gtggacttgg acgcggttct gcctactcat ggggacgcta ctaagcgtga tctgaatgcg    8700
gcggtgttcg cgggtaatga gcagactatt cttcgcaccc actaaaagcg gcataaaccc    8760
cgttcgatat tttgtgcgat gaatttatgg tcaatgtcgc gggggcaaac tatgatgggt    8820
cttgttgtgt tatctccgtc gaacggaaga tcacttcgca gaataaataa atcctggtgt    8880
ccctgttgat accgggaagc cctgggccaa cttttggcga aaatgagacg ttgatcggca    8940
cgtaagaggt tccaactttc accataatga aataagatca ctaccgggcg tatttttttga   9000
gttatcgaga ttttcaggag ctaaggaagc taaaatggag aaaaaaatca ctggatatac    9060
caccgttgat atatcccaat ggcatcgtaa agaacatttt gaggcatttc agtcagttgc    9120
tcaatgtacc tataaccaga ccgttcagct ggatattacg gcctttttaa agaccgtaaa    9180
gaaaaataag cacaagtttt atccggcctt tattcacatt cttgcccgcc tgatgaatgc    9240
tcatccggaa tttcgtatgg caatgaaaga cggtgagctg gtgatatggg atagtgttca    9300
cccttgttac accgttttcc atgagcaaac tgaaacgttt tcatcgctct ggagtgaata    9360
ccacgacgat ttccggcagt ttctacacat atattcgcaa gatgtggcgt gttacggtga    9420
aaacctggcc tatttcccta aagggtttat tgagaatatg ttttttcgtct cagccaatcc   9480
ctgggtgagt ttcaccagtt ttgatttaaa cgtggccaat atggacaact tcttcgcccc    9540
cgtttttcacc atgggcaaat attatacgca aggcgacaag gtgctgatgc cgctggcgat   9600
tcaggttcat catgccgtct gtgatggctt ccatgtcggc agaatgctta atgaattaca    9660
acagtactgc gatgagtggc agggcggggc gtaattttt taaggcagtt attggtgccc    9720
ttaaacgcct ggtgctacgc ctgaataagt gataataagc ggatgaatgg cagaaattca    9780
gcttggccca gtgccaagct ccaatacgca aaccgcctct ccccgcgcgt tggccgattc    9840
attaatgcag ctggcacgac aggtttcccg actggaaagc gggcagtgag cgcaacgcaa    9900
ttaatgtgag ttagctcact cattaggcac cccaggcttt acactttatg cttccggctc    9960
gtatgttgtg tggaattgtg agcggataac aatttcacac aggaaacagc t             10011
```